United States Patent
Landfield et al.

(10) Patent No.: US 6,420,105 B1
(45) Date of Patent: Jul. 16, 2002

(54) METHOD FOR ANALYZING MOLECULAR EXPRESSION OR FUNCTION IN AN INTACT SINGLE CELL

(75) Inventors: Philip W. Landfield; Olivier Thibault; Eric Blalock; Kuey-Chu Chen, all of Lexington, KY (US); Patrick Kaminker, Berkeley, CA (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 09/627,082

(22) Filed: Jul. 27, 2000

Related U.S. Application Data

(60) Provisional application No. 60/157,849, filed on Oct. 6, 1999, and provisional application No. 60/148,563, filed on Aug. 13, 1999.

(51) Int. Cl.[7] .................................................. C12Q 1/00
(52) U.S. Cl. ................... 435/4; 435/1.1; 435/6; 435/91.1; 435/91.2; 435/270
(58) Field of Search ........................ 435/4, 1.1, 6, 91.1, 435/91.2, 270

(56) References Cited

U.S. PATENT DOCUMENTS

| | | | |
|---|---|---|---|
| 5,535,170 A | 7/1996 | Imamura et al. | ............. 365/239 |
| 5,611,350 A | 3/1997 | John | ........................... 128/731 |
| 5,963,505 A | 10/1999 | Pomet et al. | ................ 365/239 |
| 6,040,138 A | * 3/2000 | Lockhart et al. | ................ 435/6 |
| 6,052,326 A | 4/2000 | Kashiwakura et al. | . 365/230.03 |
| 6,061,593 A | 5/2000 | Fischell et al. | ............. 600/544 |
| 6,066,163 A | 5/2000 | John | ........................... 607/45 |
| 6,109,269 A | 8/2000 | Rise et al. | .................. 128/898 |

OTHER PUBLICATIONS

Irani et al. (J of Immunological Methods (1991) 139:223–231).*
Thibault et al. (Current Opinion in Neurobiology (1995) 5: 382–387).*
Monyer et al. (Current Opinion in Neurobiology (1995) 5: 382–387).*
Sucher et al. (Neuron(1995) 14: 1095–1100).*

* cited by examiner

Primary Examiner—Kenneth R. Horlick
Assistant Examiner—Alexander H. Spiegler
(74) Attorney, Agent, or Firm—McDermott, Will & Emery

(57) ABSTRACT

A method for obtaining molecules from a substantially intact single cell is disclosed. The method differs from prior methods that obtain a variable fraction of a cell's contents and therefore cannot quantitatively estimate the number of molecules in the cells. The present method comprises isolating and harvesting a substantially intact single cell from its organ tissue comprising the steps of subjecting a tissue mass to a dissociation method so that the cells are dissociated from the tissue to expose cell bodies or cell processes, contacting a dissociated cell with a device capable of collecting the cell from the tissue substantially intact, withdrawing device with the cell attached, and then isolating or detecting the molecules in the single cell.

40 Claims, 14 Drawing Sheets

Young adult

Aged

1. PATCH FOR CELL-ATTACHED RECORDINGS

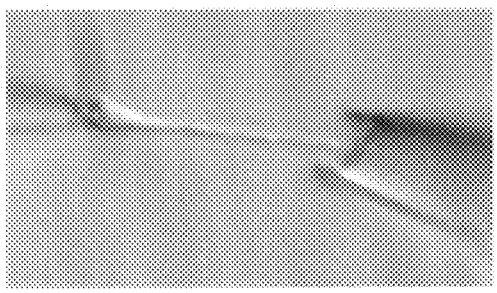
CELL-ATTACHED PATCH RECORDINGS

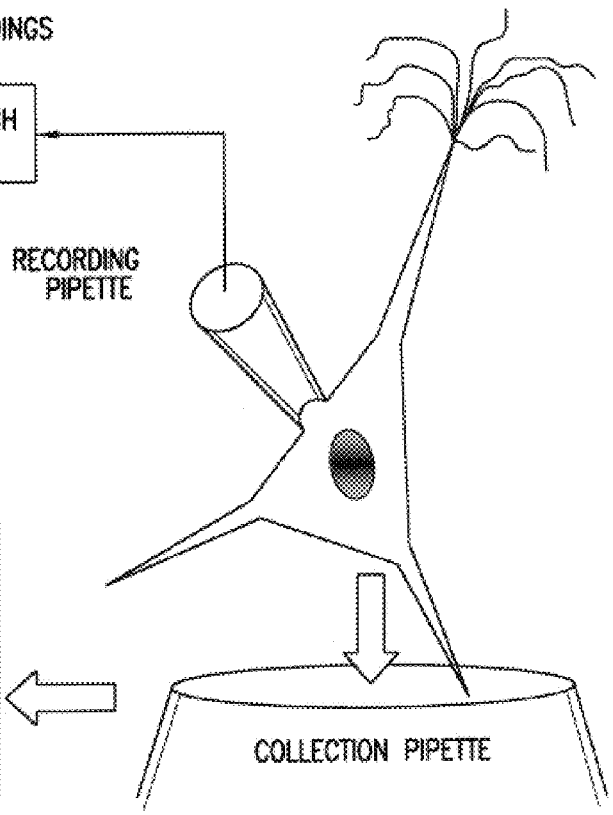
RECORDING PIPETTE

2. COLLECT CELL

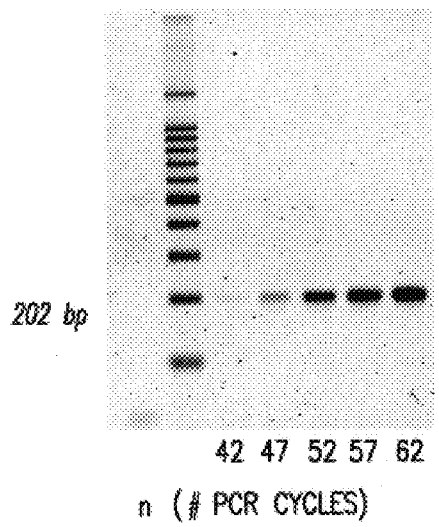

COLLECTION PIPETTE

3. TRANSFER CELL CONTENTS TO RT-SOLUTION
4. DIVIDE INTO ALIQUOTS TO RUN DIFFERENT MESSAGES
5. PCR EACH MESSAGE, OBTAINING MULTIPLE POINTS ON THE EXPONENTIALLY RISING PHASE OF PCR PRODUCT, GENERATING A LOG-LINEAR FIT ACCORDING TO:

$$Log\ N_T = n \cdot Log\ (1+e) + Log\ N_0$$

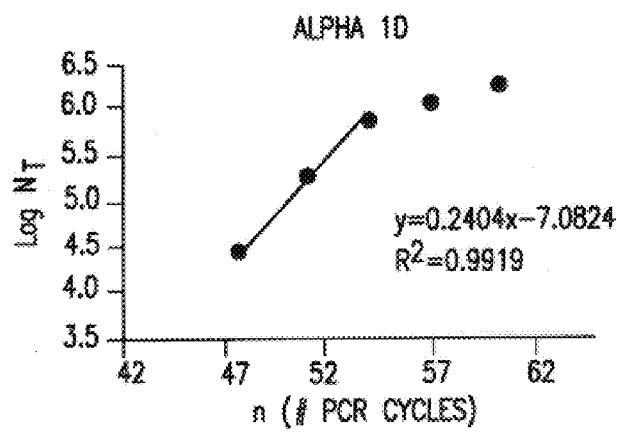

ALPHA 1D $y = 0.2404x - 7.0824$
$R^2 = 0.9919$

FIG.5

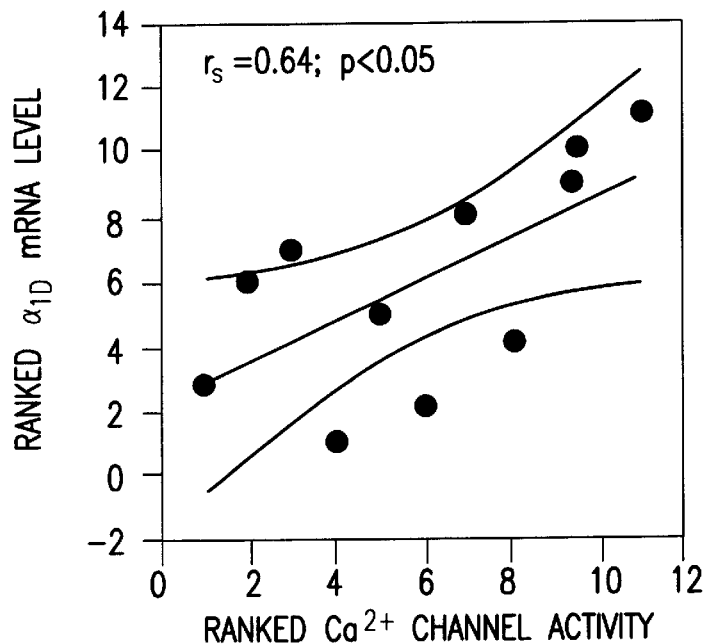
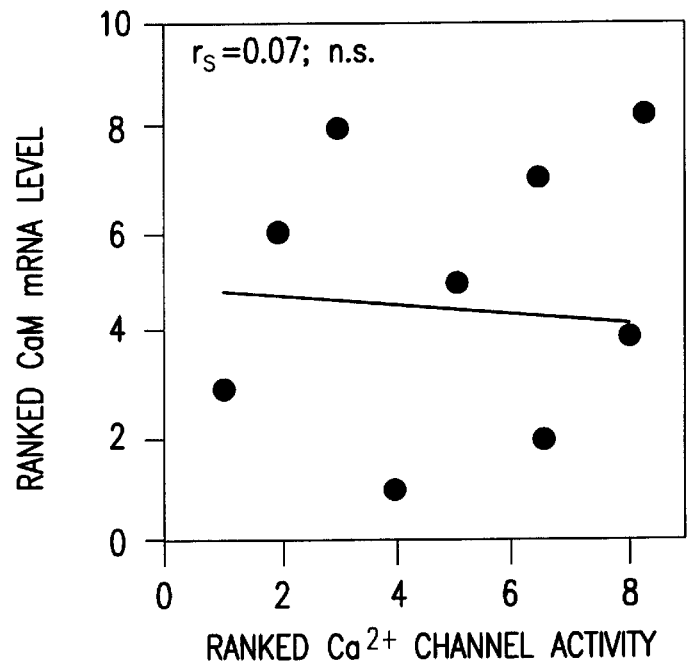
FIG.7

METHOD FOR ANALYZING MOLECULAR EXPRESSION OR FUNCTION IN AN INTACT SINGLE CELL

CONTINUING DATA

The present application claims the benefit of priority to U.S. Provisional application No. 60/148,563, filed Aug. 13, 1999; and No. 60/157,849, filed Oct. 6, 1999. The contents of these provisional applications are incorporated herein by reference in their entirety.

BACKGROUND OF THE INVENTION

1. Field of the Invention

The present application is directed to a single cell preparation method, or a brain cell preparation that provides near-optimal conditions for the accurate quantitation of gene expression in the single cell or neuron. The present invention also provides for a method for studying the functional activity in the same single cell. Also, the method of the present invention relates to the collection of a single neuron, with its membrane and dendritic processes substantially intact and with a full set of mRNA transcripts.

2. Brief Description of the Related Art

With the remarkable explosion in gene expression "chip" technology in recent years it appears that it will soon be possible, perhaps routine, to measure the expression of hundreds or thousands of genes simultaneously, under a wide variety of physiological and pathological conditions. In the foreseeable future, this new technology will clearly overwhelm our capacity to analyze the functional implications of even a fraction of the gene expression patterns that will be found. Taking the central nervous system (CNS) as an example, eventually unraveling the complex linkages between multiple gene expression and CNS function will likely require studies of physiological properties in the same neuron in which multiple gene expression is also assessed.

In turn, such studies will depend on the availability of highly specialized preparations. An optimal CNS preparation for relating gene expression to function in the same neuron should seemingly have three major attributes: 1) the ability to perform extensive functional studies on the same single neuron that is subsequently collected for gene expression analysis; 2) the ability to collect the full set of mRNA transcripts from that same neuron; and 3) the ability to collect the neuron with most of its processes intact, in order to preserve subcellular and dendritic mRNA distribution. However, the main preparations commonly used in brain studies of gene expression, including assays in homogenized tissues (RNAse protection assays, Northerns), in situ hybridization, acutely dissociated neurons, or electrophysiological recording with extraction of cytoplasmic contents (e.g., in non-dissociated slices or cultures), do not provide optimal conditions for parallel measures of function and gene expression in the same neuron. In particular, none of these approaches routinely allows for the collection of the entire cell, including such specialized cells as neurons with their dendritic processes intact. Without a full set of mRNA transcripts, accurate estimates of specific mRNA content are difficult to obtain, and specific dendritically-targeted mRNAs are lost.

Gray et al. discloses a partially-dissociated hippocampal slice (e.g., the "zipper slice" which gradually opens—or unzips—along the cell body layers) in young guinea pigs to provide improved accessibility to neurons for patch clamp pipettes. However, Gray et al. does not disclose the method of the invention whereby a substantially intact single cell is isolated whereby substantially all of the mRNA is detected.

The invention brings together technology encompassing cutting edge instrumentation for electrophysiology, confocal laser scanning microscopy (CLSM), immunoautoradiography and histochemistry, real-time detection of PCR kinetics and new DNA "chip" technology (GeneChip Scanner and Analysis Suite), to optimize and extend the invention.

While there is clearly growing recognition of the value of single cell expression-function studies in the CNS, it seems less well recognized that the preparations that are most widely available for linking function to gene expression in single cells are significantly limited in their usefulness for these purposes. For example, the physiological recording methods in which cytoplasm is extracted through a pipette, do not yield the full complement of the cell's mRNA nor do they allow correlations with topographic mRNA distribution. The proportion of total mRNA extracted varies so greatly from one cell to another that there have been few attempts to estimate the total amount of any mRNA species in a given neuron, or even to estimate relative or semi-quantitative levels. The observations based on this method to date have been generally limited to all-or-none types of findings, regarding, for example, whether or not a gene is expressed in a given cell, or in some cases, whether its ratio of expression to other genes (e.g., for different receptor subunits) is changed (e.g., Sudweeks and Twyman, 1995). In contrast, semi-quantitative or quantitative estimates of the absolute amount of expression of a gene in a cell generally requires collecting the entire complement of a neuron's mRNA transcripts. This seems particularly critical for studies on function-expression correlation in the same cells since the physiological/pathological properties of a cell (e.g., density of channels or receptors, developmental stage, biochemical phenotype or pathological change) may well reflect total level of a gene's expression rather than the ratio to another gene's expression, which might also be altered.

Values obtained with the ratio normalizing approach required when fractional cellular contents are extracted, can be substantially affected by the additional error contributed by variability in the "control" message to which the target message is normalized, by different efficiencies (e.g., in PCR) between the two messages, or by the very common occurrence in which the normalizing message is also up- or down-regulated in tandem, either by the conditions under investigation or by other conditions of the cell (e.g., size, metabolic activity) that affect both messages. The latter may sometimes provide a control for non-specific effects, but in more cases is likely to wash out the absolute value of the target gene signal with which the investigated function may be correlated. Further, it is becoming clear that differential targeting and distribution of mRNAs within the cell (e.g., dendrites or soma) play critical roles in the CNS (Steward et al., 1998; Kuhl and Shehel, 1998). The collection of mRNA by cytoplasmic extraction loses this differential distribution.

Thus, without the ability to obtain the full complement of mRNA with its topographic distribution intact, it will clearly be difficult to estimate the total amount of a mRNA species in a neuron. In turn, this will make it extremely difficult, in most cases, to draw quantitative conclusions about the relations between gene expression and physiological function in individual cells. It should be noted that although the term "gene expression" is used here as a short hand somewhat interchangeably with mRNA content, this is only for purposes of simplicity and it is well recognized that the two are not necessarily equivalent. In the present application, we focus only on the quantitation of total mRNA transcripts, but controls are of course required in many types of experiment before concluding that mRNA content directly reflects expression.

Conventional Methods for mRNA Expression Measurement in the Brain

The main available preparations are: a) Homogenized Tissues: Neuronal and glial heterogeneity generally prevents the accurate assessment of gene/mRNA expression relative to specific cell types or functions, even if small regions of brain are dissected, homogenized, and analyzed by conventional methods (RPAs, Northerns) b) In Situ Hybridization allows visualization of topographic mRNA expression in single cells, but because the tissue is fixed, does not usually permit functional measures (electrophysiology, optical imaging) from the same cells or collection of the mRNA pool for subsequent amplification; also, quantitative analysis (grain counting) is performed by sampling on one section, lending some error to the estimate of total mRNA; c) Acute Dissociation of brain neurons disrupts the membrane and amputates processes. It is not suitable for use with aged or even mature adult neurons as these are often highly traumatized by the procedure (Thibault et al., 1995a); in addition the loss of dendritic processes precludes studies of topographic differences in gene expression or collection of total mRNA; and d) Electrophysiological Whole Cell Recording (e.g., slices or culture) is compatible with many types of functional studies but generally collects mRNA by aspiration of cytoplasmic content, which as noted, is highly variable from cell to cell and prevents reliable collection of the full set of mRNA transcripts or separate study of somal and dendritic compartments. Further, the Whole-cell method dialyzes the cell's interior which can dilute substances that modify physiological function.

Thus, despite the rapidly developing sophistication in measuring multiple gene expression, the currently available preparations are not well suited for careful physiological-expression correlation studies in the same neurons or even for collecting total mRNA in a single neuron. However, as noted above, the partially-dissociated, or "zipper", brain slice (Gray et al., 1990), appears to have the potential to be a nearly ideal preparation for such studies in brain cells of mammals of any age range (Thibault et. al., 1995a; Thibault and Landfield, 1996;Chen et al., 1998 and *Preliminary Data*).

Function and Expression: Statistical Value of Single Cell Correlations

It is becoming increasingly clear that there is considerable variability in the expression responses of different neuron types in the same brain region and even among different neurons of the same type. For example, it has been found that different neuron types and/or neurons of the same general phenotype can exhibit very different quantitative or topographical (dendrites vs. soma) patterns of distribution of the same mRNA species. One recent major study concluded that there are no general rules for mRNA localization that apply to all neuron types nor are there neuron-type-specific mechanisms that invariably regulate mRNA distribution (Paradies and Steward, 1997).

Thus, testing a hypothesis that some aspect of gene expression is directly linked to a specific function will in many cases require correlational analyses of the degrees of association across these highly variable individual cellular patterns. Statistically, individual-sample correlation of course provides a more rigorous test than co-variance among group means, since the degrees of freedom (df) across which a possible correlation can vary in a study of, say, 20 neurons in which both a physiological process and mRNA content are measured in response to a treatment in each neuron, would be 19 [df=n-1(20-1)]. However, if functional and expression values are obtained separately in different neuron groups (e.g., one set of neurons for recording, and one for mRNA), then the physiology-mRNA correlation can only vary around the number of experimental conditions (group means) and the associated degrees of freedom (e.g., treatment or no treatment). Therefore, the many more df's generally found in an individual sample correlation study allow for clear statistical inferences and probabilistic statements on the amount of variance in one variable that is accounted for by variance in the other. This is not possible for associations involving few df's (e.g., typically across group means) which are consequently more susceptible to chance associations.

A more general problem in this regard is that most major treatments or conditions (e.g., aging, seizures, intense synaptic stimulation, lesions, drugs, hormones, neurodegenerative disease, developmental stages, etc.) presumably activate a large number of genes. As the new microarray techniques for simultaneously assessing thousands of genes increasingly come on line, it will become extremely difficult to determine which if the many observed changes in expression are relevant to function without careful same-cell observations of both function and expression. Thus, the application of function-gene expression correlations in single cells (e.g., with large multiple regression correlation matrices and appropriate controls for performing many comparisons) may become one of the key first steps in attempting to interpret widespread gene activation in relation to function and in dealing with the vast quantities of data that the field is on the threshold of obtaining.

Prior Studies on Electrophysiology and Single Cell RT-PCR

The vast majority of previous studies on electrophysiological recording and RT-PCR in the same single neurons have, as noted, addressed all-or-none or message ratio questions, usually related to whether or not a cell expresses a specific mRNA, and, if so, whether or not it also manifests a particular physiological property. For example, the GABAA receptor is thought to be composed of 5 subunits, but there are almost 20 known subunits and variants that can form the GABAA receptor. In transfected cells, different combinations can influence affinity, pharmacological modulation, channel conductance and single channel kinetics (e.g., Porter et al., 1992). However the actual subunit combinations that occur in vivo are not known. Consequently, many single cell recording-PCR studies have been used to determine which subunits are expressed in which cells, and how these combinations affect function (Sudweeks and Twyman, 1996).

Although several prior studies have attempted semi-quantitative analyses, a recent report (Tkatch et al., 1998) indicated a quantitative correlation between an electrophysiological function ($K^+$ channel A-currents) and a measure of gene expression for a related subunit (mRNA for the Kv4.2 $K^+$ channel) in individual brain neurons. However, that study was performed in acutely dissociated basal ganglia neurons and therefore could not collect total mRNA. In addition, a few studies in peripheral or invertebrate neurons have also quantitatively correlated physiological function and gene expression (e.g. Baro et al., 1997). But no one has accomplished the isolation of a single cell neuron having complexes processes as in an embodiment of the present invention.

There is clearly an overall paucity of CNS single cell studies of electrophysiological function-gene expression correlations, very likely because of the limited availability of preparations compatible with quantitative analyses.

The Partially-Dissociated ("Zipper") Slice. The partially-dissociated slice preparation (often termed the "zipper slice" for its tendency to gradually open, or unzip, along the cell body layers), was originally developed by Gray, Johnston and colleagues (Gray et al., 1990) in young guinea pigs. The partial dissociation (unzipping) procedure involves mild enzymatic exposure to proteolytic enzymes and gentle "shaking" (FIG. 1). It provided unparalleled access to brain neurons for small patch pipettes and therefore yielded the high quality recordings needed for single channel analyses, with very little disturbance of cell structure. This adaptation incorporated somewhat shorter and lower enzyme exposure and more gradual "unzipping" (Thibault et al., 1995a), and required several months to optimize. Of particular importance was that the yield of high resistance (>20 G$\Omega$) recordings from healthy neurons was equivalent from young adult, mid-aged and aged rat slices (Thibault and Landfield, 1996). Thus, with this preparation, we were able to carry out the first single channel analyses in brain neurons of aged mammals, and found an aging-related increase in the estimated membrane density of available L-type voltage sensitive $Ca^{2+}$ channels (VSCC) (Thibault and Landfield, 1996) (FIGS. 2, 3).

Although each preparation has advantages for certain kinds of electrophysiological studies, it was noted above that neither the acutely dissociated cell preparation nor the non-dissociated slice or culture preparation permits consistent collection of the entire mRNA complement in a single cell. Aspiration of cytoplasmic contents through a whole cell patch pipette, in either of these preparations yields a varying and unknown fraction of the mRNA content from cell to cell (e.g., significant mRNA is likely trapped by organelles or the collapsing cell structure, and most dendritic mRNA is probably trapped in collapsing dendrites).

Moreover, most current electrophysiological preparations are extremely limited in their usefulness for applications to mature adult, much less aged, animals. Cell cultures generally utilize embryonic or postnatal neurons and acute dissociation techniques are usually focused on juvenile animals. In fact, we found that acute dissociation was so traumatic for aged rat brain cells that almost none survived the dissociation procedure (Thibault et al., 1995a). Even most non-dissociated slice studies are performed on juvenile or very young adult animals (cf. reviews, Thibault et al., 1995a; 1998a).

In the zipper slice however, the neuron that is being recorded with a cell-attached pipette can be easily and gently extracted from the slice, with nearly all of its processes intact simply by gradually withdrawing the pipette while still maintaining negative pressure on the cell body. The entire long apical dendritic tree slides readily out of the slice still attached to the non-disrupted cell body. Most of the basilar dendrites also appear to be intact (FIG. 4). Aged animal neurons are extracted as readily and as non-traumatically as are young. Thus, not only is the zipper slice particularly suitable for large scale single channel recording studies, but it appears to be a neurobiological preparation that can provide a fully intact neuron with its morphological structure preserved, for analysis of gene expression. Although this preparation has usually been used with hippocampus, there appears to be no reason why the preparation would not work from essentially any brain region, or with any tissue of an animal in an animal of any age.

Another method that can yield semi-quantitative estimates of mRNA expression in a single neuron that is largely topographically intact is in situ hybridization. However, even this approach generally yields only a sample of total mRNA (i.e., on the section through the cell) and can only be related to functional measures of the same cell with difficulty.

Limitations of the Zipper Slice

Although the zipper slice is presently extremely well suited for ion channel and imaging studies (cf. below), its main limitation appears to be its sub-optimal suitability for synaptic studies. The weakening of synaptic and tissue connections that makes it so ideally suited for cell extraction also results in variable synaptic connections, and therefore the zipper slice yields inconsistent results in synaptic studies. However, the present invention overcomes this limitation and greatly expands the range of functional studies for which the zipper slice is highly valuable.

SUMMARY OF THE INVENTION

A method is described for isolating a single cell from its organ tissue, usually a neuron from neural tissue, while causing minimal disruption of the cell's processes and membrane. The method of the invention comprises extracting that cell from the tissue mass, washing and transferring the cell, and then collecting the entire cell. In the case of neurons, the processes are substantially intact.

The method of the invention further comprises determining the presence or amount of nucleic acid that is present in the extracted single cell. The inventive method comprises collecting the entire cell into a small pipette or tube filled with solutions and substances that facilitate the detection by amplification or hybridization of the messenger ribonucleic acid (mRNA) transcripts. The cell membrane is then disrupted and methods for amplification and art-accepted measurement techniques for measurement of small quantities of mRNA or deoxyribonucleic acid (DNA) are applied.

In a preferred example, a brain slice from an experimental animal is placed in a perfusion chamber and kept alive by oxygenation and artificial cerebrospinal fluid (ACF). The slice is then subjected to mild enzymatic concentrations and is nicked (cut) in a way such that gradual dissociation of the slice occurs along the cell body layers. Gentle vibration enhances this dissociation.

When the dissociation has proceeded sufficiently to expose cell bodies, one of the cells is "patched" onto a glass patch pipette (electrode) using standard patch clamp recording procedures. These procedures involve suction (negative pressure) in the pipette, and result in a tightly formed seal between the cell membrane and the tip of the pipette. This tight seal facilitates low noise amplification and recording of the electrical activity of the cell.

After the recording or other physiological monitoring session is completed, the cell is then pulled out of the tissue slice with most of its processes intact by maintaining the suction pressure of the pipette (electrode) and withdrawing the pipette by use of its micromanipulator controls. The cells remain attached to the pipette tip and readily slide out of the tissue mass with this method. The nerve cell on the tip of the pipette is optionally washed in clean ACF to remove extraneous mRNA and it is then transferred to a larger collection or harvesting pipette filled with an appropriate reverse transcriptase (RT) solution. The membrane is then disrupted osmotically to allow the RT process to begin. The contents of the cell are then transferred again to a tube containing an appropriate solution for amplification, for example, by polymerase chain reaction (PCR). Other methods for amplifying mRNA or DNA would be equivalent to RT-PCR for purposes of the invention.

These and other objects of the invention will be more fully understood from the following description of the invention, the referenced drawings attached hereto and the claims appended hereto.

BRIEF DESCRIPTION OF THE DRAWINGS

FIG. 5 shows a summary of the steps involved in collection and molecular analysis of a recorded cell. 1) Enzymatic treatment (see methods) partially frees neurons from tissue, providing unobstructed access of the recording pipette to the cell membrane; 2) The cell is gently puled free of the tissue and collected. 3) The collected cell is transferred to a reverse transcriptase (RT) solution; 4) Subdivided into aliquots; 5) Each aliquot can then be amplified for specific messages.

FIG. 7 shows that correlation between channel activity and message level is specific for the message of interest. Top. Relationship between $Ca^{2+}$ channel activity and $Ca^{2+}$ channel $\alpha_{1D}$ mRNA level across individual neurons. A significant positive correlation ($r_s$=0.64, p<0.05, Spearman's nonparametric test) was found between L-type $Ca^{2+}$ current and $\alpha_{1D}$ mRNA level (estimated by SC RT-PCR) across individual cells. On the vertical axis cells were ranked according to mRNA level. On the horizontal axis the same cells were ranked according to channel activity. Bottom. Lack of correlation between $Ca^{2+}$ channel activity and calmodulin (CaM) mRNA level. No significant correlation ($r_s$= 0.07; n.s.; Spearman's nonparametric test) was found between CaM mRNA level and L-type $Ca^{2+}$ channel activity in the same cells as Top. (From Chen et al., 1998).

Figure 1:
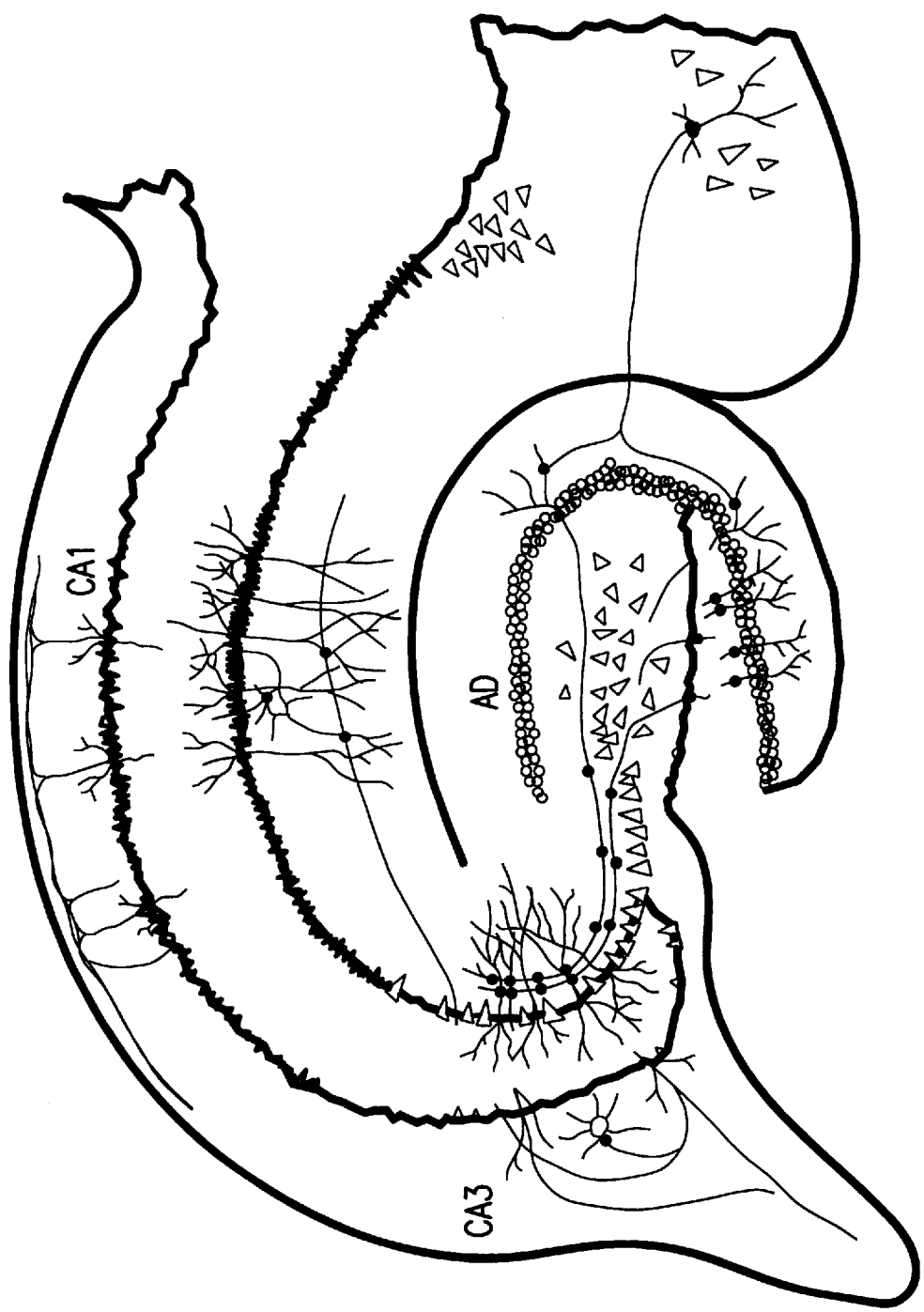
FIG. 1 shows a schematic drawing of the hippocampal "zipper slice" split along the major cell body layers. (From Gray et al., 1990).
Figure 2A:
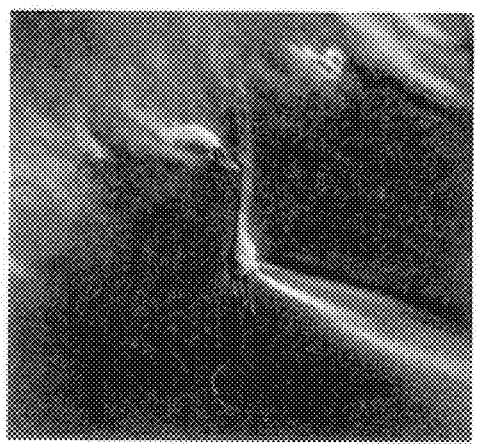
FIGS. 2A–2D show a zipper slice preparation for recording single $Ca^{2+}$ channels from CA1 neurons from a young (A) and aged (B) hippocampal slices. (C) and (D) show five depolarizations to +10 mV as well as the average current ensembles below. Ensembles were created from 15 such depolarizations. (From Thibault and Landfield, 1996).
Figure 2B:
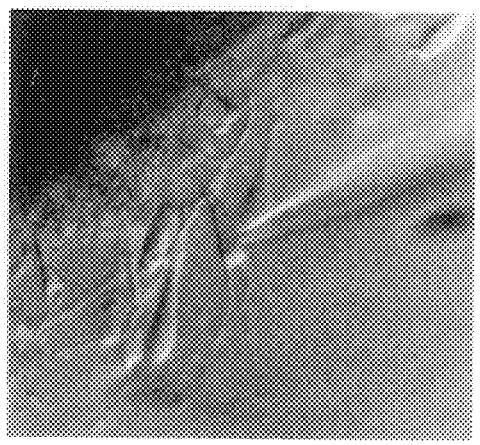
Figure 2C:
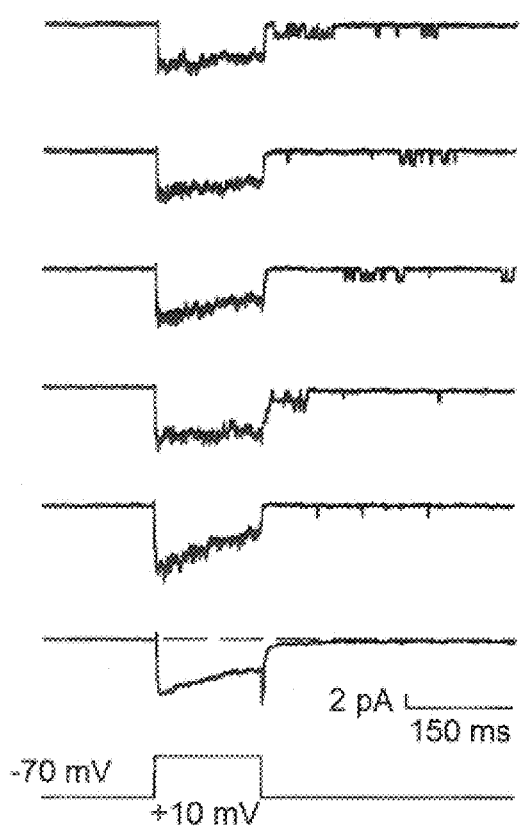
Figure 2D:
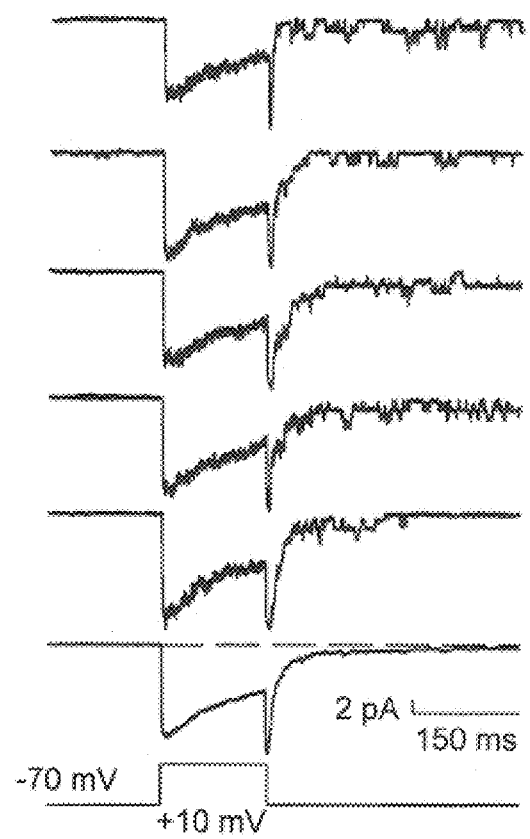
Figure 3:
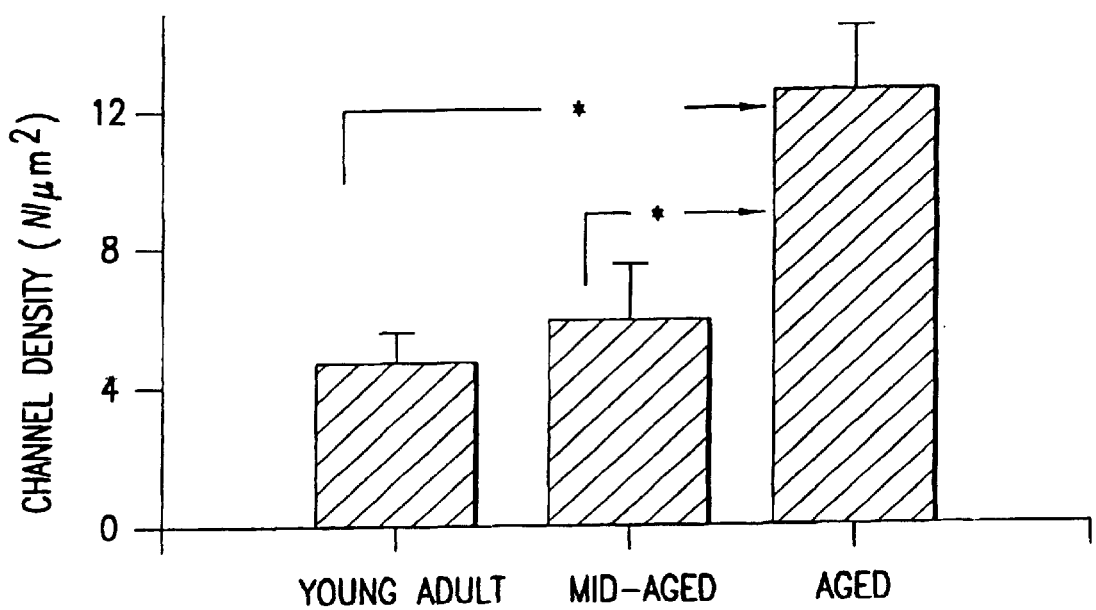
FIG. 3 shows that L-type channel density was obtained by estimating N from maximum simultaneous openings and calculating patch area from pipetted resistance. Channel density increased with aging (p<0.001) (n=19–35/group). (From Thibault and Landfield, 1996).
Figure 4A:
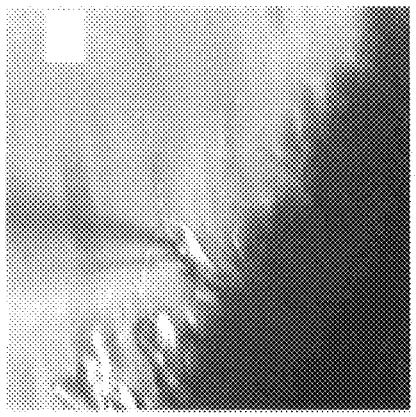
FIGS. 4A–4D show harvesting cells with intact neurites. A) The recording electrode is patched onto a CA1 pyramidal neuron and electrophysiologic data is recorded. B) The cell is then pulled from the slice using the recording electrode (note intact dendrites). C) The cell is cleaned of tissue debris by placing it at the inlet port of the perfusion chamber, where uncontaminated bath solution flows into the chamber. D) The apical dendrite is drawn into the collection pipette by capillary action. Following this, position pressure applied to the recording pipette releases the cell in the collection pipette. (From Blalock et al., unpublished).
Figure 4B:
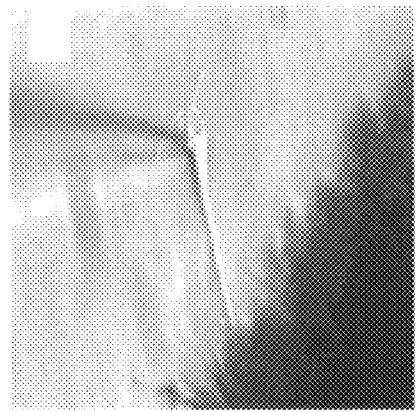
Figure 4C:
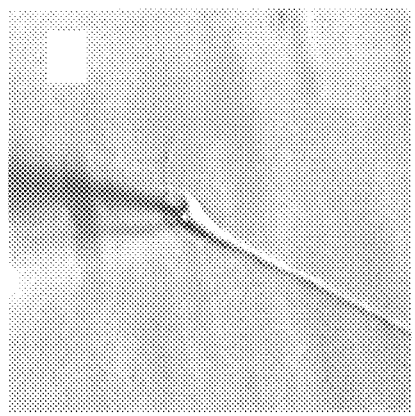
Figure 4D:
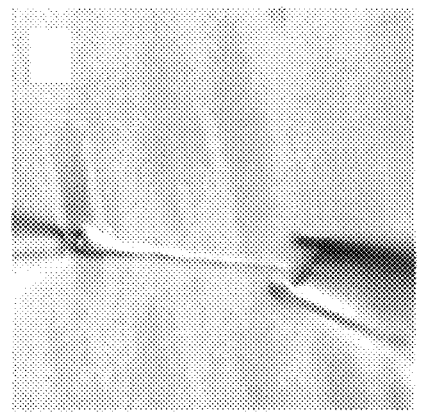

With the neuron's membranes potential voltage clamped at −70 mV, transection of the large process did not cause disruption of the recording configuration, or alter the whole-cell $Ca^{2+}$ currents. Similar results have been obtained in many other neurons. (From Thibault et al., 1995b).

DETAILED DESCRIPTION OF THE INVENTION

Many studies have examined RT-PCR or other methods of amplification of mRNA or DNA contents of a single brain cell after recording procedures (see review in Monyer and Lambolez, 1995; Sudweeks and Twyman, 1996; and Mackler and Eberwine, 1993). However, all of these prior studies have either extracted the internal contents of the cell by aspiration, after breaking the membrane, or used acute dissociation procedures to isolate the cells. Unlike the partial dissociation method used in this application, the acute dissociation procedures massively disrupt the cell's plasma membrane and amputate most of its processes (Kay and Wong, 1982).

A significant aspect of the invention is the adaptation or partially dissociated tissue (e.g., slices) for the new use of gene/mRNA expression analyses as well as a method for cell transfer and preparation that works to provide accurate estimates of the relative numbers of an mRNA transcript type within a single physiologically characterized brain cell.

The invention is directed to a method for extracting a single cell from a complex intertwined biological tissue without massively disrupting its structure and/or its plasma membrane. The major advantage of this method for any molecular or biochemical analysis of molecular contents of the cell is that the entire set of the cell's mRNA transcripts or other molecular species is captured. Conventional methods inevitably lose some of the contents during aspiration or acute dissociation, because of leakage after membrane disruption, collapse of the cell's structure and trapping of contents, loss of large processes and other causes. This loss of molecular contents is variable and unknown from cell to cell and therefore all measures of contents obtained by these conventional procedures must be normalized as ratios to other substances of the cell. The other substances are usually very heterogenous (e.g., total RNA) or are potentially subject to different and variable forms of regulation than the substance of interest (e.g., another mRNA species). This technical problem adds great additional sources of variation to single cell measures of mRNA collected by conventional means, and therefore has been one major impediment to detailed quantitative analyses in single neurons.

The method of the invention has the important advantage over conventional methods in that it allows the collection and amplification of the full cell contents of a molecular species and therefore, provides the potential for more accurate measurement of single cell molecular content. Moreover, many tissues are heterogeneous and contain diverse cell types, which is particularly true for the Central Nervous System (CNS), and therefore, measurement from tissue homogenates can be confounded. The ability to measure accurately the molecular contents of a single cell will circumvent this problem of this confounding heterogeneity.

Further, a second recognized advantage of being able to measure single cell contents is that it confers the ability to correlate gene expression of a cell, for example, with the physiological function or other phenotype of the same cell, thereby greatly facilitating the analysis of functional consequences of gene expression. With the rapid advent of new technologies for measuring expression of thousands of genes at a time (e.g., DNA chip technology) the ability to determine which are most closely correlated with function and phenotype will be increasingly important.

A third major advantage of the method of the invention is that it captures the cell with its molecular contents still distributed anatomically within the cell in a topographical pattern similar to that found in vivo. This is because the cell structure has not collapsed and the processes are intact. In neurons, for example, it is increasingly recognized that protein synthesis can occur in dendrites and that the mRNAs found in dendrites are different quantitatively from those found in the soma (Steward et al, 1998). Therefore, obtaining the entire neuron with dendritic processes intact will greatly facilitate the detailed analysis of molecular regulation in different regions of the cell, which will enhance the understanding of the function of dendritic mRNA.

Although the method has been developed in the brain, and seems particularly well suited for CNS studies, it is to be understood that the invention is not limited to isolation of neurons. The inventive method can be applied to the isolation of a single cell from any tissue source, such as, kidney, endocrine glands, and so on. Any use of a gentle partial dissociation procedure and capture of a complex single cell with its processes substantially intact and without membrane disruption, or disruption of the processes, with the goal of more accurately quantifying the content and/or distribution of a molecular species in a cell are encompassed by the invention.

The invention has been developed initially and validated for mRNA of specific genes, but the application of these procedures for accurate measurement of any molecular species, including proteins, lipids or other biochemical substances are encompassed by the invention.

The invention also encompasses any variation in which a neuron or other complex cell type was collected and then specific parts of that cell were dissected, amputated or isolated, for purposes of selectively measuring molecular contents in the dissected component or fraction.

The present invention is also directed to a novel use of partially dissociated tissues for collecting and measuring an entire neuron largely intact and with its full set of molecular contents. The present application also describes new methods for achieving this by extracting and collecting an individual cell without substantially disrupting its membrane. The present application provides evidence and describes procedures showing that this use is feasible and reliable. In particular, the present invention also describes methods for dissecting dendritic parts of an extracted neuron. These methods for extracting, washing and transferring a cell have been validated in our laboratory by showing that RT-PCR of the mRNA contents for a $Ca^{2+}$ channel gene is highly consistent across different cells and also correlates semi-quantitatively with phenotypic expression of the appropriate $Ca^{2+}$ channel. Thus, the present inventors are the first to propose and illustrate the collection of the entire contents of a largely undisrupted cell from a complex tissue such as the CNS.

One aspect of the invention is to define optimal conditions of enzymatic exposure (concentration, duration, oxygenation, temperature, etc.) that allow single neuron extraction from multiple brain areas with the least disturbance of mRNA content. Single cell PCR and in situ hybridization will be run in parallel to cross-validate the conclusions. Three to five $Ca^{2+}$-regulatory genes (mRNA) will be examined in adult and aged rats and subsequently, mice.

Another aspect of the invention is to develop optimal methods for examining mRNA and protein content in the same zipper slice neurons, by taking alternate sections for in situ hybridization and immunoautoradiography. In other studies, a single neuron will be extracted from a zipper slice gently placed on a coated glass slide and fixed and strained with antibodies. Two methods for studying mRNA in the same cell will also be compared: in situ hybridization or RT-PCR, in both rats and mice.

Another aspect of the invention is to extend the range of functional studies for which the zipper slice can be utilized by developing new techniques to "unzip" the slice after the functional studies are performed rather than before, as is presently done. The major advantage will be that functional studies can then be performed before synaptic contacts are altered by even the mild enzymatic exposure of the current method. Two methods will be compared for finding and extracting the same recorded cell after the partial dissociation procedures: 1) loading with $Ca^{2+}$-sensitive dye during recording (before partial dissociation), and finding that same cell on the CLSM after partial dissociation; and 2) maintaining pipette contact with the cell after recording is completed, during subsequent gentle dissociation in the recording chamber. Once this technique is established in rats, are extended directly to mouse slices.

Another aspect of the invention is to develop methods to separate dendritic and somatic morphological compartments for independent PCR analyses. Several methods of dissecting the apical dendrite away from the soma and cutting it into separate pieces are compared.

Still another aspect of the invention is to extend the single cell RT-PCR approaches of the invention to new technologies for large scale expression profiles by adapting and validating methods for amplifying the mRNA pool of a single cell. We develop proportional amplification of mRNA transcripts to a degree that will be compatible with large scale expression profiling using both new "DNA chip" microarray technology and a 96-well PCR format. Technology such as real-time PCR, TaqMan®, ABI PRISM 7700 Sequence Detection System, and laser-activated DNA microarray reading techniques such as GeneChip Scanner, Workstation, may be practiced with the invention.

Hippocampal mRNA by In Situ Hybridization and RPA

Recent studies in our laboratories perhaps provide an example of the additional statistical power that single cell correlations can lend to the process of scientific inference. We adapted the zipper slice preparation and found clear evidence of an increase in the average membrane density of L-type voltage-sensitive $Ca^{2+}$ channels (VSCCs) in CA1 cells of aged rats relative to young-adult or mid-aged rats (Thibault and Landfield, 1996; please see Appendix). Subsequently, in a series of experiments with in situ hybridization and ribonuclease protection assays (RPAs), the latter in homogenized hippocampus, we found that mRNA content for the $\alpha_{1D}$ pore-forming subunit of the L-type VSCC also increased with age in rats (Herman et al., 1998; please see Appendix). In addition, these studies suggested a possible rise in the $\alpha_{1C}$ variant of the L-type subunit, but no change in mRNA for the $\beta_{1B}$ subunit (Herman et al., 1998). These mRNA data in vivo closely echoed similar data from hippocampal cultures, which showed an increase in $\alpha_{1D}$ mRNA over age in culture that paralleled an increase in L-VSCC (Porter et al., 1997).

An increase in membrane density of available ion channels can arise from increased synthesis of channels, but it can also reflect a new availability of previously silent channels (e.g., activated by intracellular signaling processes such as phosphorylation, co-factors, etc.). Although the finding of increased $\alpha_{1D}$ mRNA was suggestive that new synthesis was involved in our findings on L-VSCC, the similar direction with aging of group mean values for channels and for mRNA clearly did not provide sufficiently strong evidence for the conclusion that the increased L-VSCC probably depended on increased gene expression. Several factors can of course compensate for an increase in mRNA without increasing net protein content (e.g., more protein turnover, and protein content does not necessarily equate with functional channels). Moreover, the results showing changes in multiple L-VSCC subunit messages ($\alpha_{1D}$ and $\alpha_{1C}$) reemphasized the more general problem that, even if the increase in L-VSCC did arise from new expression and synthesis, it would not be possible to determine whether this was likely due to increased expression of $\alpha_{1D}$ or $\alpha_{1C}$, or both, or perhaps to an altered expression ratio of one of the α subunits to β.

Single Cell RT-PCR

As discussed in Background of the Invention, correlation analyses in single cells not only provide stronger statistical evidence that an observed mRNA-VSCC linkage is not coincidental, but in addition can clarify which of the many altered messages may be most closely correlated with the altered function. For these reasons, we determined to direct a major effort toward the development of techniques that would allow us to test the $\alpha_{1D}$ mRNA and L-VSCC correlation, as well as other function-expression correlations, in single neurons. To take advantage of our ability to harvest the full complement of mRNA transcripts from neurons in the zipper slice, we invested much effort and resources in the development of highly accurate message amplification techniques of specific mRNA species from single neurons.

Initially, two basic approaches were compared: the "linear amplification" method (Eberwine et al., 1992) vs quantitative PCR (Monyer and Lambolez, 1995). However, in several cases we were interested in relatively rare messages (e.g., the $\alpha_{1D}$, the glucocorticoid receptor (GR)), and therefore we chose, after initial comparisons, to focus on the PCR method (FIG. 5).

Our earlier work with ribonuclease protection assays (RPAs) and in situ hybridization had required constructing multiple probes and optimizing conditions for each of the specific messages in which we were interested. Many of our studies have focused on the hypotheses that brain aging and age-related neuropathology are associated with altered $Ca^{2+}$ homeostasis (Landfield et al., 1992; Thibault et al., 1998a) or that glucocorticoids, and perhaps other steroids, modulate brain aging by altering $Ca^{2+}$ homoeostasis (Kerr et al., 1989; Landfield et al., 1992). Consequently, many of the genes in which we are interested are related to $Ca^{2+}$ regulation or steroid receptors. In our previous RPA and in situ studies, we developed and validated primers and probes for 11 genes ($\alpha_{1D}$, $\alpha_{1C}$, VSCC β subunit, calmodulin, calbindin D, cyclophilin A, GR, mineralocorticoid receptor (MR), plasma membrane $Ca^{2+}$-ATPase (PMCA) isoforms 1 and 2 and glyceraldehyde dehydrogenase (GAPDH), the latter as an abundant control. All have been validated for RPAs in homogenized tissues and in situ hybridization (please see Herman et al., 1998 and Porter et al., 1997-for Methods). At this point, new message probes can be developed and added to the repertoire fairly routinely.

As we moved into single cell work, however, the conditions for each primer had to be optimized again for single cell PCR. Moreover, in validating the single cell PCR techniques it was critical to confirm three points: 1) the same message could be amplified with relatively similar efficiency in different cells; 2) the relative rank order of samples for the expression of a given message was consistent in tests run on different fractions of those samples; and 3) the estimates were proportional to the fraction of sample loaded from a given cell.

After these points were confirmed and RT-PCR conditions were optimized (e.g., two-step of PCR for some mRNAs, a single gel band for each target gene, consistent amplification efficiency patterns, etc.) we established standard procedures and criteria for assaying a message in a single cell (FIG. 5). These are: to be included in data sets, mRNAs must show efficiencies (rates of rise) within a specified range; each sample must have a full kinetic analysis across PCR cycles (to ensure that measures are taken from a cycle on the exponential phase, rather than at saturation) and the same cycle for all samples (cells) being compared in an experiment must be run on the same gel.

Single Cell Correlations of Electrophysiology and Expression

Figure 6:
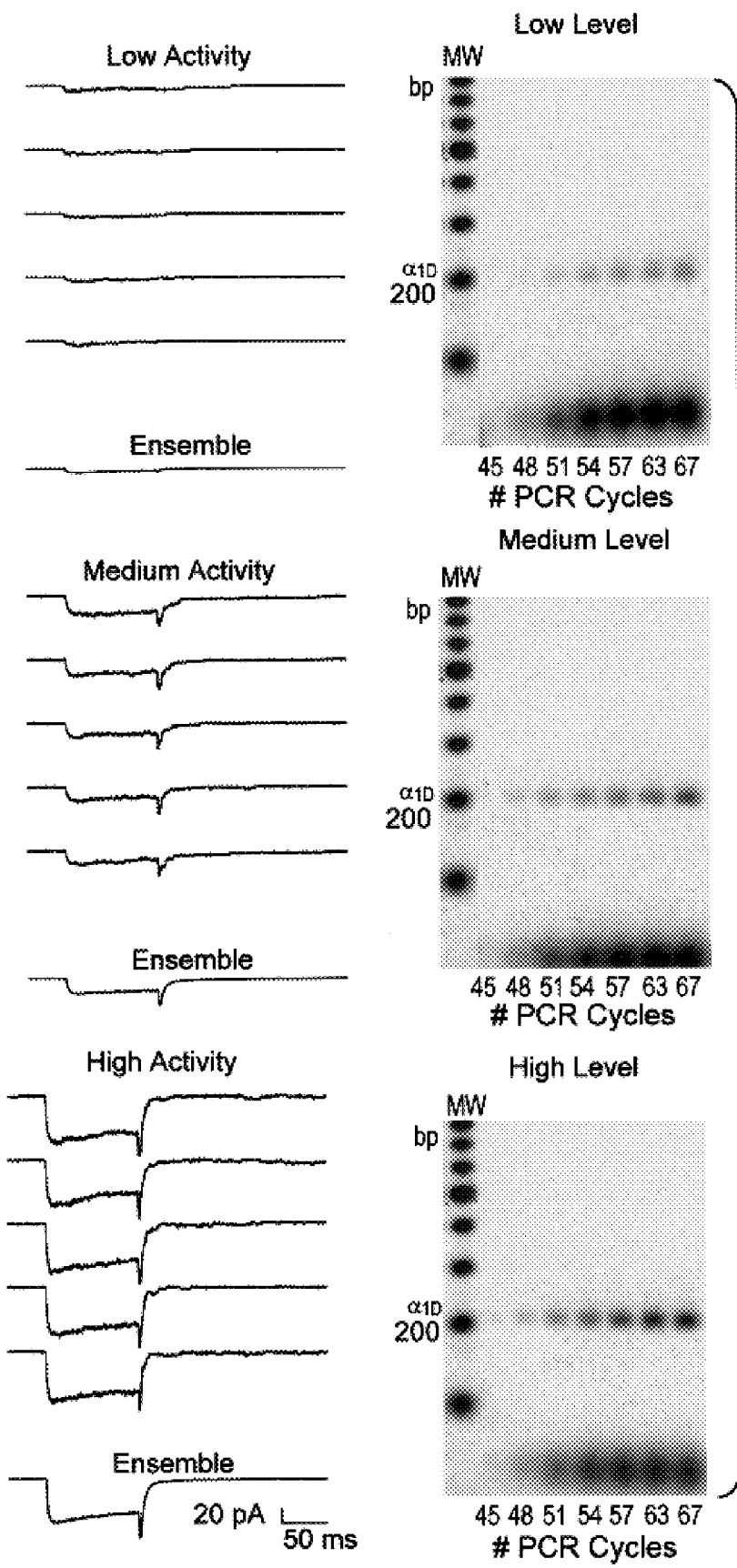
FIG. 6 shows $Ca^{2+}$ channel activity and $\alpha_{1D}$ subunit mRNA expression are associated. Representative on-cell patch L-type $Ca^{2+}$ channel activity (left) and $\alpha_{1D}$ mRNA gels (right) show the 3 levels of electrophysiologic activity and mRNA expression (note a 202 bp $\alpha_{1D}$ band at $45^{th}$ and $54^{th}$ cycle #). Top. Low levels of channel activity are associated with low levels of expression. Middle. Medium levels of channel activity are associated with medium levels of expression. Bottom. High levels or activity are associated with high levels of expression. (From Chen et al., 1998).

The procedures outlined above enabled us recently to complete two major studies comparing $\alpha_{1D}$ mRNA content with electrophysiological analyses of L-VSCC in the same individual neurons. As shown in FIG. 6, there appears to be a striking correlation from one of these studies between number of L-type channels in the patch and $\alpha_{1D}$ expression in the same cell. FIG. 7 shows the semi-quantitative (rank order) correlation from one of these studies between membrane density of L-VSCC and $\alpha_{1D}$ PCR product in 11 adult/aged pyramidal neurons, quantified on a phosphorimager at a PCR cycle in the exponential rising phase of the amplification curve (all cells compared on the same cycle on the same gel). (Non-parametric rank order correlation statistics were used because the cells were highly variable, particularly on electrophysiology (FIG. 6), and were not distributed normally on either variable). FIG. 7 (bottom panel) also shows that similar analyses for calmodulin gene expression from the same cells found no indication of correlation.

Thus, although these single cell studies (Chen et al., 1998 and in prep.; Blalock et al., in prep.) obviously do not prove a causal link between $\alpha_{1D}$ gene expression and L-VSCC levels, they provide much stronger statistical evidence for an association than was available from our separate independent analyses in groups (e.g., Thibault and Landfield, 1996; Porter et al., 1997; Herman et al., 1998). Further, these apparently represent the first semi-quantitative correlations between electrophysiology and expression in non-disrupted brain neurons.

Moreover, it should be noted that, while these studies have been extraordinarily demanding and time-consuming (e.g., each message, each sample and each validation procedure requiring a separate gel and several days), new real-time sequence detection analyzer (ABI PRISM 7700-Perkin Elmer) can be used, which allows simultaneous PCR amplifications in 96 wells and provides an on-screen view of the PCR kinetics, efficiency and specific product. Thus, the time-consuming preparation of gels will be circumvented and many more samples can be run with greater sensitivity and accuracy of quantification. This will clearly provide a major boost to the rate at which these studies can be carried out.

Figure 8A:
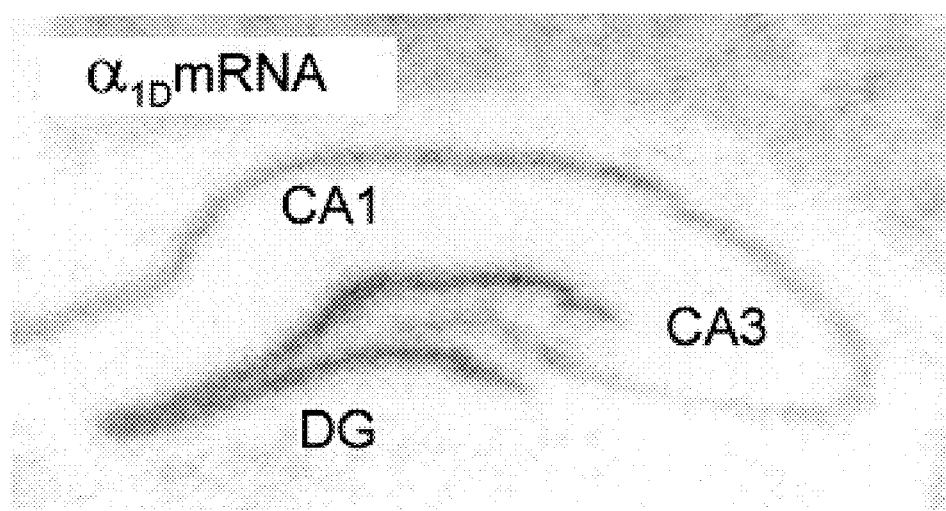
FIG. 8 shows the localization of the $\alpha_{1D}$ mRNA (in situ hybridization, ISH) and protein (immunoautoradiography, IAR) in adjacent hippocampal sections. Note the extensive overlap of signal for mRNA and protein in the two sections, and the correspondence of the relative intensities of ISH and IAR in dentate gyrus (DG) vs CA1 and CA3.
Figure 8B:
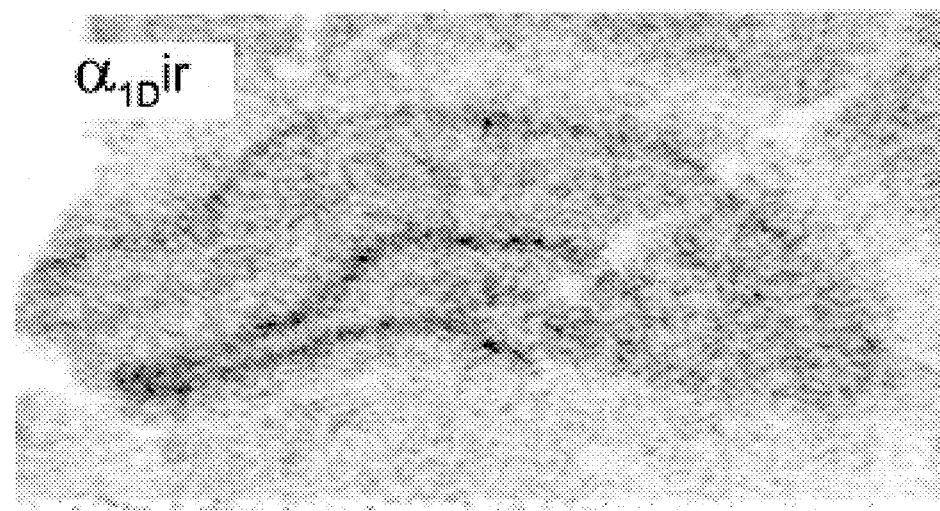
Figure 9A:
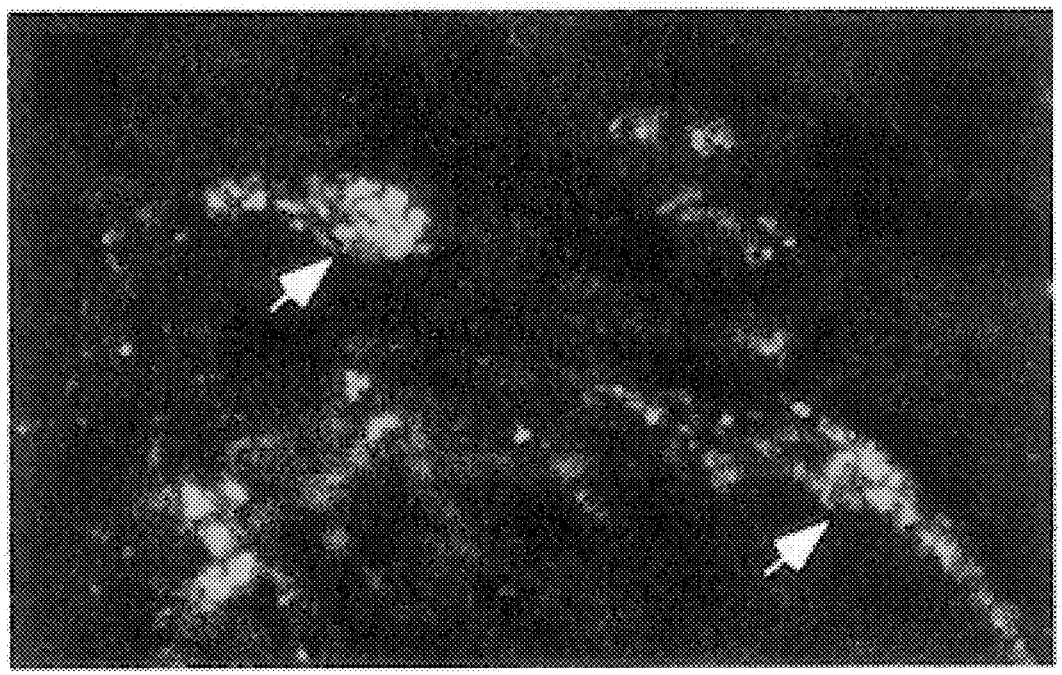
FIGS. 9A–9B show confocal microscopic analysis of $\alpha_{1D}$ immunoreactivity in 0.5 µm optical sections from hippocampal slice preparations. Panel A illustrates an example of a confocal image of two distinct cells in CA3 (arrows). Images show punctate immunoreactivity localized in the cell cytoplasm and membrane regions. Frequency distribution (B) of single-cell fluorescence intensity from 0.5 µm optical sections. All measures were taken from cells wholly contained within the thickness of the tissue section, and were sampled from the optical section containing the greatest staining area from the cell.
Figure 9B:
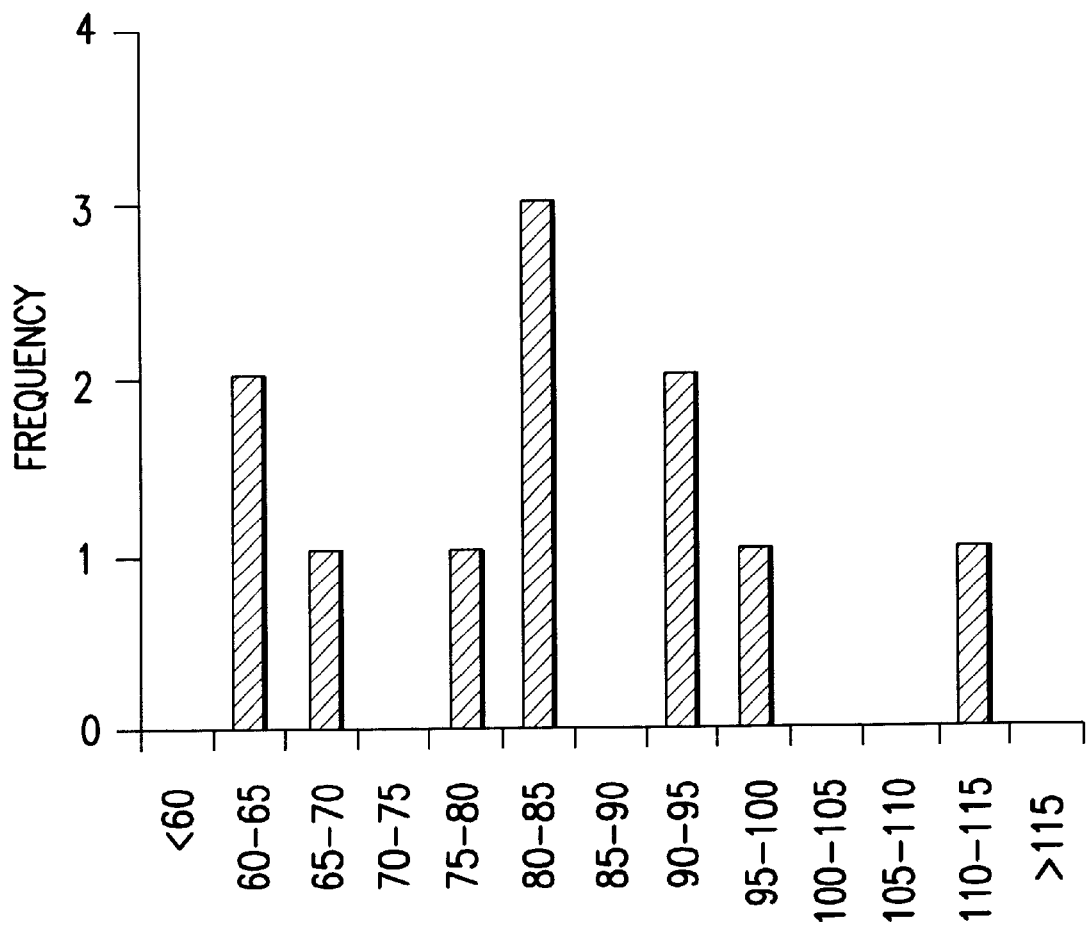

Localization of $\alpha_{1D}$ VSCC mRNA and Protein in Hippocampus: Immuno-autoradiography and Imunofluorescence An important aspect of being able to assess function in the same cells in which gene expression is quantified, of course, is the ability to evaluate protein content of those cells. Consequently, we have been working to develop cellular measures of protein content in the same cells as those in which mRNA is evaluated. At present, we can consistently take alternate serial sections for mRNA (in situ hybridization) and protein measures (immunoautoradiography). At least for the $\alpha_{1D}$ subunit, there appears to be a reasonable correspondence. FIG. 8 illustrates the localization of $\alpha_{1D}$ subunit mRNA and protein in hippocampus. Note the high degree of overlap between signals demonstrated using cRNA probes and $\alpha_{1D}$ antibody, consistent with likely co-localization. Note also the proportionally high expression of both $\alpha_{1D}$ mRNA and immunoreactivity (ir) in the dentate gyrus. FIG. 9 demonstrates localization and semi-quantitation of $\alpha_{1D}$-ir in individual neurons of a hippocampal slice preparation, visualized using immunofluorescence. Single cells within the slice have variable levels of $\alpha_{1D}$-ir, suggesting differential quantitative protein content in individual neurons.

There are multiple means of collecting a neuron once it has been loosened from its tissue connections. Therefore, any method in addition to the tight seal-forming pipette technique that is used to draw a largely intact neuron or other single cell from partially dissociated tissue in order to collect its essentially full set of molecular contents for purposes of analyzing some molecular or biochemical properties, would also be a variation on this invention.

The invention is directed to molecularly analyzing the full contents of a single neuron or other cell type that has not been substantially disrupted during collection, such that analyses of molecular/biochemical process will be more accurate. A general method that can achieve this is to gradually and partially dissociate the enveloping tissue, such that connections are weakened sufficiently to allow the extraction and collection of the single cell without the massive disruption of membrane and loss of contents that occurs when presently available conventional methods are used for collection of molecular contents from a single cell. The example provided herein was of extraction and collection by a patch pipette and a collection pipette. However, since the main basis of the invention is the novel concept of collecting a largely intact single cell for molecular/biochemical analyses of its full contents, any method of extraction, including use of a larger suction pipette, a sharp dissecting needle or any other instrument capable of collecting the cell from partially dissociated tissues without major cellular disruption, would be a variation of the invention.

The single cell isolation method of the invention is applicable to any tissue, preferably the brain region in animals of any age, including, but not limited to, guinea pigs, rats, mice and humans.

The following examples are offered by way of illustration of the present invention, and not by way of limitation.

EXAMPLES

Basic 'Zipper' Slice Procedures

Because the zipper slice procedures will be used for essentially each Example, they are outlined briefly below. More targeted or specialized methods/procedures are described under the individual Examples.

Conventional Slice Methods. Slices will be prepared using standard methods, as previously described (Thibault et al., 1995a). After rapid removal of the hippocampi, a central section of each hemisphere is transected perpendicular to its axis and mounted onto the stage of a vibratome (Vibratome series 1000). Slices are cut (300 $\mu$m thick) in standard artificial cerebrospinal fluid (ACSF) and transferred to a 35 mm dish using a fire-polished Pasteur pipette. Standard ACSF consists of (in mM): 114 NaCl, 30 $NaHCO_3$, 10 glucose, 2.5 KCl, 2 CaCl and 8 MgCl. The slices are transferred to an interface-type chamber (35 mm dish containing 2.1 mg pronase per 3 ml of oxygenated ACSF), placed inside an incubator at 31.5° C. The dish is continuously perfused with moist oxygen/$CO_2$ gas mixture (95% $O_2$2/5%$CO_2$).

Zipper procedure. The slices will be placed in a warm (31.5° C.) oxygenated 35 mm dish containing 2.1 mg of pronase per 3 ml of ACSF. After approximately 30 minutes, the contents of the 35 mm dish will be replaced with 1.6 mg thermolysin in 3 ml of warm oxygenated ACSF. After 20 minutes in thermolysin, a slice is then washed several times and transferred to an analyzer cup containing $Ca^{2+}$-free ACSF (ACSF without $Ca^{2+}$ and 2 mM EGTA) and gently shaken. Periodic visualization of the slice on the stage of a microscope (or the CLSM) allows evaluation of the progress of the "unzipping" process. After cell bodies are visible they are then placed in a recording chamber and patched onto for recording and harvesting for mRNA analysis (FIG. 2).

Figure 10A:
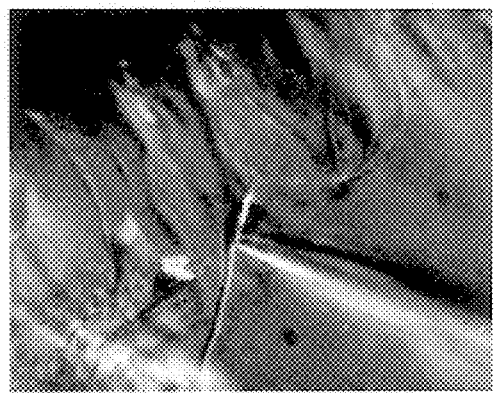
FIG. 10 shows capturing cells from the zipper preparation. A) Cell soma and neurites are well exposed by enzymatic treatment and $Ca^{2+}$ channel activity is recorded. B) Post-recording the cell is gently pulled away from the slice and C) collected with a harvest pipette.
Figure 10B:
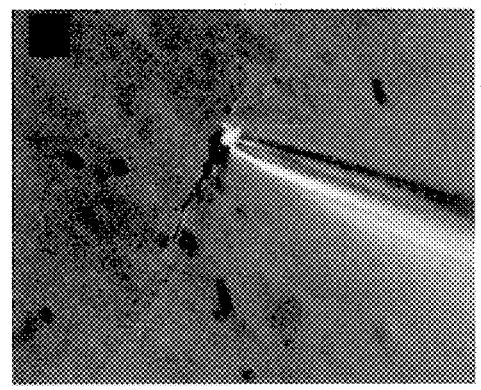
Figure 10C:
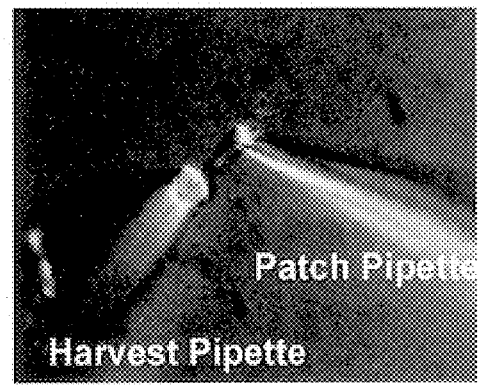

Harvesting an intact cell. As noted, we have developed a reliable technique for harvesting an intact neuron using patch pipettes, micromanipulators and a collection pipette. Using a cell-attached patch pipette, the cell of interest is first gently teased away from the rest of the slice (FIG. 10). The high resistance seal formed between the glass and the cell membrane is used to physically pull the cell away from the slice. This cell is washed with a continuous flow of clean ACSF before being harvested. A second, larger pipette (collection pipette) is then lowered into the recording chamber. The collection pipette is empty and thus "draws" the cell by capillary action into its lumen. The capillary action is controlled by a luer-lock system placed on the back end of the collection pipette (FIGS. 4, 10). The contents of the collection pipette are then analyzed by RT-PCR analysis for estimates of expression of specific genes of interest.

Example 1

Optimal Conditions for mRNA Analysis a. Rationale: Previous work by Gray et al. (1990) and by ourselves has established that neurons are quite healthy and viable in the zipper slice preparation. Moreover the close correlation of $\alpha_{1D}$ mRNA with L-VSCC in individual cells (FIG. 7), which generally agree with in vivo data from animals (Herman et al., 1998), suggests that mRNA content is not much altered by our standard zipper slice procedure.

However, it may well be that under some conditions of preparation (e.g., last slice of the day) there is deterioration of physiological function and/or mRNA content. If this preparation is to be used widely, it will be important to obtain the baseline parametric responses, and to determine the optimal procedures as well as limitations on its use. Markers and criteria for health should also be defined. Thus, the main factors that regulate the zipper process are systematically varied (duration, enzyme concentration, oxygenation and temperature) and mRNA content assessed as a function of this variation. The working technical hypothesis for this Example is that, for each factor, an optimal range exists such that mRNA will most closely approximate values seen without any dissociation procedures.

b. Design: The overall design of this Example will involve sequential experiments to systematically vary each of four main factors; each factor will be varied in turn while the others are held constant. After an optimal value is found for one factor (e.g., duration) that value will be used while other factors are varied. Each factor will be studied initially in 5 young adult (3–5 mo old) and 5 aged (27 mo old) male rats (F344×BN Hybrids).

The basic design involves incubation of slices from 30–120 min in enzymatic solution. Slices will be collected for analysis before incubation and every 30 min thereafter to 120 min, slices collected at each incubation point will be placed in a holding chamber and then collected from the holding chamber at 3 hr, 4 hr and 5 hr after the start of the incubation.

Half of the slices at each time point will be processed for in situ hybridization (ISH) and half will be placed in the recording chamber for collection of individual cells for subsequent PCR analyses. In both the in situ and the PCR studies, three mRNA species will be analyzed simultaneously: $\alpha_{1D}$ $\alpha_{1C}$ and calmodulin. Because the in situ analyses can be compared to slices taken at the zero time (prior to any enzyme exposure), the time course of changes in cellular mRNA content for 3 messages can be examined. The effects of varying enzyme exposure as well as holding duration will be quantified (by grain counting in ISH and PCR for single cells). It should also be emphasized that single channel recording data will also be obtained for many of the cells studied by PCR.

Thus, these studies will determine whether duration of enzyme exposure or holding affects measures of mRNA, and also whether this effect varies with age. If little effect on mRNA is found, this will indicate relative resistance of mRNA content to these procedures and permit considerable latitude in experimental design. On the other hand, if mRNA is found to decline after some critical period, then this information will be of great importance for future studies with this preparation.

It should be emphasized that the RT-PCR analyses of single cells cannot be compared to a zero time point, or perhaps to the 30 min point because some minimum of enzymatic incubation is necessary to unzip the slice and expose the neuronal somata. However, at each time point thereafter, the PCR estimates can be compared to ISH estimates at the same time points. Although the measurement scales of these two methods will differ, the patterns of change over time can be tested for their degree of correspondence.

After exposure duration is determined, an exposure point that is sufficient for unzipping the slice, but causes the least alteration in mRNA for any of the messages either adult or aged rat neurons, will be used for examining the effects of varying enzyme concentrations in 10 other rats (5 young, 5 aged).

Using a design similar to that above, slices will be cut and placed in varying enzyme concentrations in 8 different combinations (e.g., low Pronase-low Thermolysin, low Pronase/high Thermolysin, high Pronase/low Thermolysin, high Pronase/high Thermolysin, as well as high or low Pronase/normal Thermolysin and high or low Thermolysin/normal Pronase (high Pronase=1.5 g/l; low Pronase=0.33 g/l; normal Pronase=0.67 g/l; high Thermolysin=1.33 g/l; low Thermolysin—0.25 g/l; normal Thermolysin=0.5 g/l). Under each condition, slices will be collected for both ISH and PCR.

These studies will clarify much more systematically than our original development studies the minimum amount of enzyme needed for unzipping, and the maximum that can be tolerated without altering mRNA levels. This is important since higher concentrations permit more rapid unzipping and lower concentrations are presumably less disruptive. The interactions of enzyme concentration and aging will also be clarified by these studies.

A similar series will also be carried out in 10 other animals to examine the effects of temperature and some studies will also test the rate of mRNA decay with low oxygenation.

Although 5 animals are proposed for each condition, it is likely that more will be needed because of failed experiments or variability or subtlety of the results, or the need for some pilot tests; therefore an extra 20 young adult and 10 aged animals are requested (Totals: 35 young, 25 aged animals).

c. Methods: The ISH methods required for this Example are described in Example 2 below, along with methods for concomitant analyses of protein content in these same tissues. The methods for recording and preparation of the zipper slice are described earlier (please see above) (for further detailed description of our slice preparation and recording protocols, please see Thibault et al., 1995a; Thibault and Landfield, 1996).

Example 2

Concomitant Protein Analyses in Slices and Single Cells a. Rationale: Although the expression of protein in a cell is not always directly reflective of gene expression, in many cases it can be a critical index of function that is relevant to gene expression. Thus, as we develop more sophisticated approaches for measuring gene expression in a single cell, it would clearly be highly valuable to also obtain semi-quantitative estimates of proteins in the same cell. Moreover, just as it is critical to optimize and examine the limits of conditions for mRNA content (Example 1), similar parametric studies are needed for protein evaluations. The present Example is directed at conducting immunoautoradiographic (IAR) and immunohistochemical (IHC) analyses of $\alpha_{1D}$ protein content in the same slices and neurons as will be analyzed for mRNA in the various conditions studied in Example 1 above. In addition, a new technique will be developed for plating a single cell that has been extracted from the slice, but is still on the tip of the recording pipette (FIGS. 4, 10). The cell will be lowered onto a polylysine-coated microscope slide and plated with the use of positive pressure through the pipette. Once plated, the single cell will be fixed, stained for protein content by IHC and evaluated by CLSM. Same single cell will also be evaluated by one of two methods to be compared: 1) subsequent collection of the cell for RT-PCR analyses (e.g., as in Cheetham et al., 1997); or 2) ISH of the fixed cell.

Even if both techniques for assessing mRNA eventually prove too inconsistent or are unreliable, this new method for evaluating protein in a single cell from a zipper slice will be a valuable addition to our ability to assess function and gene expression, as it will provide a means for testing the correlation between protein content and physiological measures. In turn, these physiological measures can be related back to mRNA expression (single cell PCR) in other neurons.

Analysis of Protein in Single Neurons Extracted from the Zipper Slice

This experiment will employ confocal microscopic analysis of $\alpha_{1D}$ subunit protein expression in single rat and mouse cells processed for electrophysiological analysis using the zipper slice technique. Following electrophysiological recording, the target neuron will be gently lifted from the slice preparation by the recording pipette and repositioned over a polylysine coated photo-etched coverslip. The cell will be transferred to the coverslip by gentle positive pressure. The cell will be allowed to adhere to the coverslip for 2 hours, at which point the coverslip will be transferred to a 24 well culture plate and frozen at −80° C. until analysis.

Immunohistochemistical staining of tissue will be performed as above. In each immunohistochemical run, 8–10 recorded cells from each group (young and old animals) will be processed simultaneously. Histological sections of whole hippocampal slices from the same animals will be processed in parallel, to provide positive controls for staining and to allow correlation of single-cell data with whole tissue analysis. In each run, controls will include single cells processed with: 1) omission of primary antibody; 2) omission of secondary antibody; 3) preabsorption with peptide/protein, if available.

Immunohistochemical data will be analyzed semi-quantitatively. Briefly, fluorescence intensity will be integrated across the cell through summation of values obtained in 0.5 μm optical slices (using confocal microscopy). Integrated intensity values will be obtained for each of 8–10 cells/group. The relationship of staining intensity (in fluorescence units) to $Ca^{2+}$ channel density will be evaluated by regression analysis, allowing correlation of protein staining with $Ca^{2+}$ currents both within and across age groups.

Note that mRNA levels will also be assessed in these same cells, either by single-cell RT-PCR or the FISH method for mRNA quantitation. At present, these experiments are designed to systematically assess the $\alpha_{1D}$ VSCC. To the extent feasible in the available time, we will implement parallel sets of analyses to assess expression of other target proteins. In addition, we are currently attempting analysis of two or more protein species in individual neurons using dual label immunofluorescence methods. Should this technique prove reliable and reproducible, we will include co-localization analysis of $\alpha_{1D}$ (or alternative regulated proteins) and housekeeping proteins (e.g., GAPDH).

It appears likely that relative fluorescence intensity measures will allow suitable resolution of protein expression for correlation with electrophysiological measures recorded in the same neuron. However, should fluorescence intensity prove an unreliable measure of protein levels, we will employ IAR analysis/grain counting to assess single-cell expression in an analogous fashion.

d. Anticipated Outcomes: We anticipate that serial section analysis will provide accurate estimates of relative levels of mRNA and protein expression in single neurons in hippocampal slices. The use of both radioisotopic and fluorescent applications should provide cross-methodological validation of the individual techniques and thus reinforce the interpretation of the data derived from each technique. It should be noted that non-radioactive ISH is generally less sensitive than radioisotopic labeling. For abundant proteins, detection by FISH should not be problematic; however, less abundant mRNAs may present sensitivity problems that may require resolution by additional amplification steps. If this is the case, we will attempt alternative labeling protocols (e.g., biotin labeling with or without biotinylated tyramide amplification (see Speel et al., 1998; Speel et al., 1999; Raap, 1998; McKay et al., 1997).

The use of mouse tissue for hippocampal slice methods has been discussed previously (see Example 1). The mouse $\alpha_{1D}$ subunit has been cloned (Perez-Reyes et al., 1990), and a mouse cDNA suitable for will be generated by RT-PCR by our laboratory (see Herman et al., 1996). Further, given the overwhelming sequence homology of rat and mouse $\alpha_{1D}$ mRNA (94%), it seems likely that the polyclonal $\alpha_{1D}$ antibody can be used to assess protein expression in mouse hippocampus.

Example 3

Techniques to "Unzip" the Slice After Functional Studies Rather than Before a. Rationale and Design: As noted, the zipper slice preparation already provides an excellent preparation for a wide range of electrophysiological (e.g., single ion channel) and imaging studies. However, the utility of the zipper for synaptic studies is limited substantially by the weakening of synaptic connections during partial dissociation which may be one reason the preparation is not more widely used. Therefore, to greatly extend its potential usefulness for functional studies, this Example is directed at the examination of two new approaches for unzipping the slice after functional studies. In the first approach, individual cells in the intact non-dissociated slice will be impaled with a sharp electrode containing a Ca2+-sensitive indicator (Indo-1). Indo-1 fluorescence will be used to label the cell so that it can be found again after partial dissociation. Although many indicators should work in these kinds of studies, it will be advantageous to uses a ratiometric $Ca^{2+}$-sensitive dye during these early developmental studies to determine rapidly whether any of our procedures are inducing toxic elevations of $Ca^{2+}$ (from influx or internal stores). During this period, extensive physiological measures will be acquired [e.g. after hyperpolarization (AHP), synaptic input-output curve, $Na^+$ spike threshold, LTP, etc.]. Immediately following these measures, the sharp electrode will be withdrawn and the slice will be exposed to enzymes and "unzipped". After the cell layer opens, that same cell will be identified on the CLSM, recaptured with a cell-attached patch pipette and harvested for mRNA analysis. The second approach will be developed in parallel studies. In this approach, we will utilize the patch clamp, rather than the sharp pipette configuration in the non-dissociated slice and no indicator dye will be used. Once a patch is formed, a wide range of physiological studies will be carried out. Following these, contact will be maintained with the cell (monitored by a high resistance seal) during the subsequent exposure of the slice to enzymatic digestion. Gentle mechanical "teasing" will be used to unmask the cell, which will then be gently extracted and harvested as previously described. In both approaches, the goal will be to perform functional synaptic studies before exposure to enzyme and to then find and collect the same cell after unzipping.

b. Methods, Approach #1: Electrophysiological Intracellular Recording and Cell Loading. CA1 pyramidal neurons will be impaled with sharp recording micro-pipettes. The electrode tips are standardly back-filled with 14 mM Indo-1 in 150 mM Potassium methylsulphate (KMeSO4) and 10 mM Hepes buffer (pH 7.2). The rest of the electrode shank is back-filled with 2 M KMeSO4 in 40 mM Tris-based buffer (pH 7.2). The pipettes generally manifest resistances between 90–150 MΩ when filled with indicator-containing solutions. The neurons consistently exhibit input resistance (IR) between 50 and 100 MΩ. Current clamp recording will be carried out with an Axoclamp 2A (Axon Instruments) in bridge mode. Cells will be held at −70 mV with a minimal holding current of 0.1–0.3 nA and Indo-1 allowed to diffuse into a neuron over a period of ~10 minutes, during which baseline electrophysiological measurements (AHP, input resistance, synaptic input/output (I/O) curves, $Na^+$ spike threshold) will be acquired. Synaptic activation is will be accomplished with a bipolar stimulating electrode made from teflon-coated stainless steel wires and placed into stratum radiatum (Schaffer-Commissural pathway) approximately 200–300 μm from the recorded cell.

Figure 11:
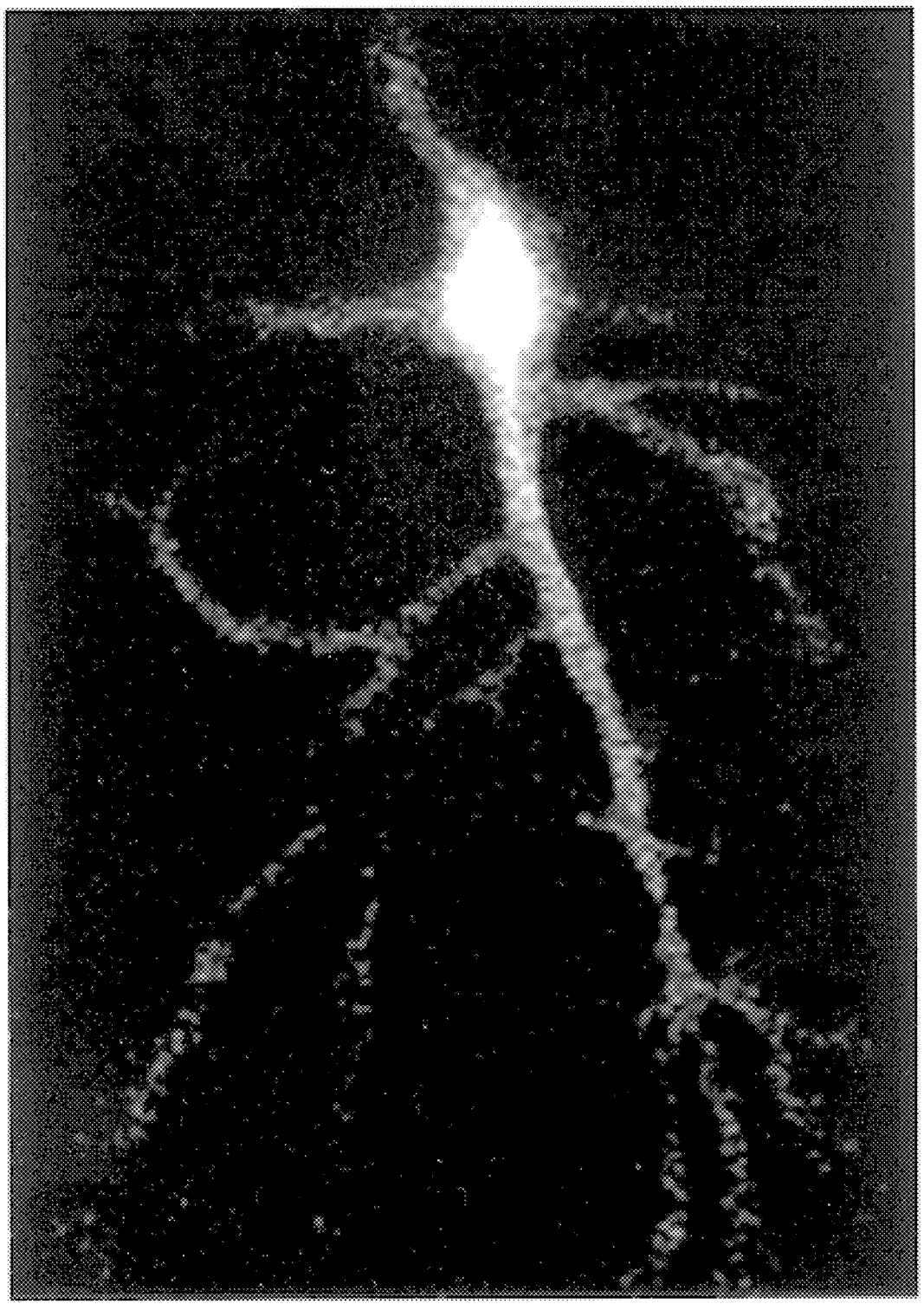
FIG. 11 shows Indo1 loaded CA1 neuron in an intact slice. Image reconstructed from multiple transients. 30
Figure 12:
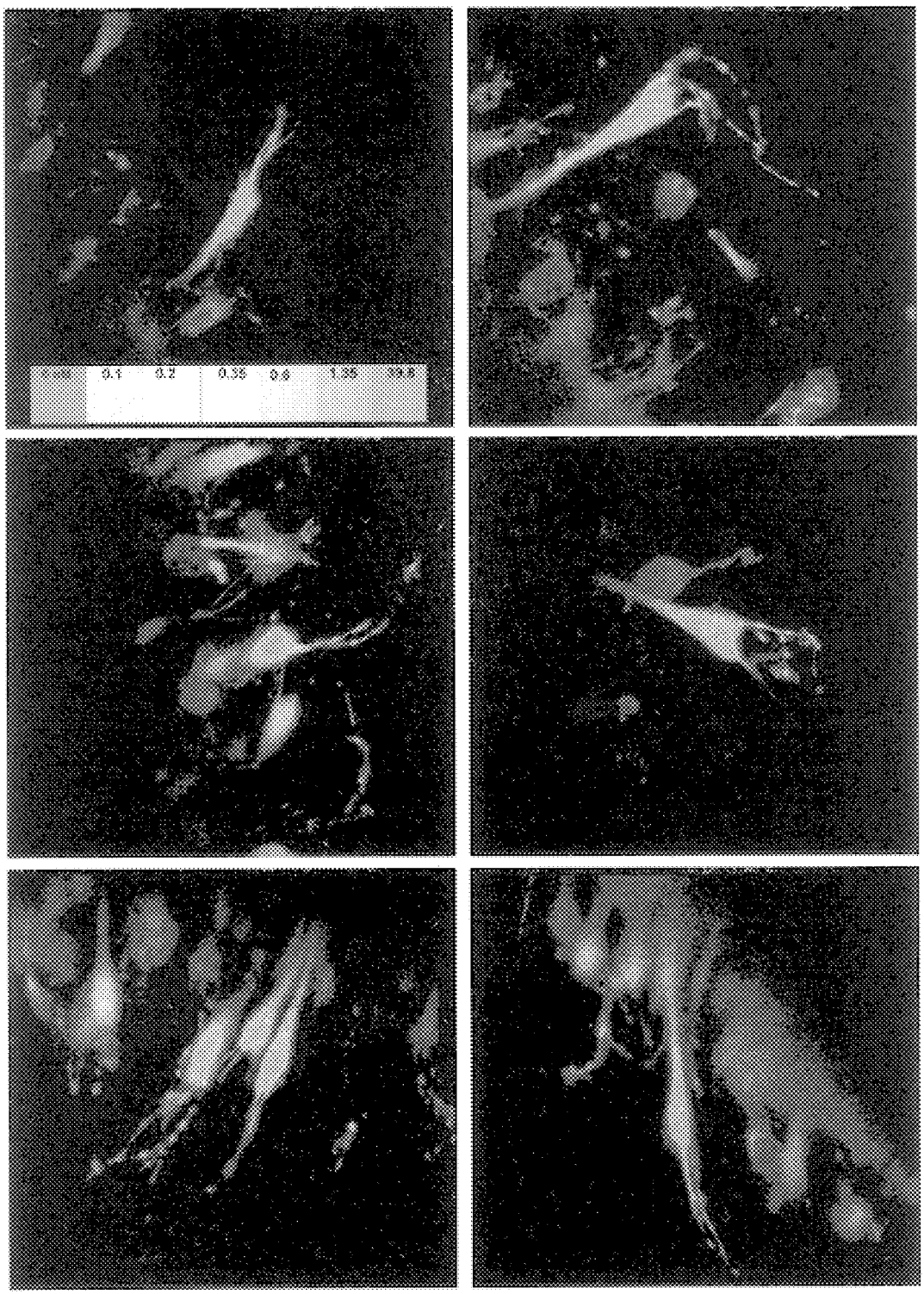
FIG. 12 shows examples of Indo1-AM-loaded CA1 neurons in the "zipper" slice preparation.

LTP induction paradigm and electrode removal. Once cells have been loaded with indicator and baseline electrophysiological measurement have been taken, half will be subjected to a long-term potentiation (LTP) protocol. In these, the synaptic pathway will be tetanized (5 sec at 50 Hz) at 150% of $Na^+$ spike threshold. $Ca^{2+}$ imaging measures and EPSP values will be acquired during this protocol and at 5 minutes interval thereafter for the following 20 minutes (FIG. 11). At this point the sharp electrode will be removed from the cell. This sharp pipette withdrawal technique is not anticipated to be traumatic to the cell as the membrane is known to reseal almost instantly, leaving behind sufficient indicator to identify the cell at a later point. It should be noted that this type of electrode removal approach has been used successfully in a number of imaging studies (e.g. Tank et al., 1988; Guthrie et al., 1991). In these experiments, cells were loaded with indicator using sharp electrodes and the pipette was then removed from the cell to permit better $Ca^{2+}$ imaging by closer apposition of the objective or even by "flipping" the slice for study on an inverted microscope. In all of those studies, measures of resting $Ca^{2+}$ appeared to be within the normal physiological range (~80 nM). Once the pipette is withdrawn in our studies, the slice will then be transferred with a fire-polished Pasteur pipette into a 35 mm dish to begin our standard enzymatic zipper procedure. Subsequently, the slice will be returned to the CLSM stage, and the indicator loaded neuron will be identified (FIG. 12). That neuron will then be patched onto with a cell-attached pipette (Axoclamp 2A, Axon Instruments) and extracted from the slice (e.g., FIGS. 4, 10). Again, the advantage of using cells loaded with a ratiometric indicator is that at any point following the opening of the cell layer, the cell can be monitored for toxic $Ca^{2+}$ levels. Moreover, it is possible that LTP-activated cells will show elevated $Ca^{2+}$. Because no recording will be performed at this stage, the seal quality does not have to be excellent, which will improve our yield considerably. Once collected, each cell would be assessed by RT-PCR for three mRNAs. In an effort to improve on the preparation and to minimize enzymatic exposure, we will determine the lowest concentration of each of the enzymes necessary to find the loaded cell, based in protocols proposed in Example 1.

These same studies will be carried out on hippocampal slices from young-adult and aged animals (5–7 and 27–29 months old, respectively) (40 animals per age group over two years). After these procedures are systematized, we will also pursue the same experiments in hippocampal preparations from C57BL/6J mice of analogous ages. We propose to accomplish this by decreasing the enzymatic concentrations and/or finding the right compromise between cell accessibility and enzymatic digestion.

b. Methods, Approach #2: Maintaining Patch Contact

Throughout the Zipper Procedure. As an alternative to withdrawing the pipette from the cell while unzipping of a slice, we propose to also examine an alternative approach in which a cell would be patched onto and recorded from before dissociation, but thereafter patch contact would also be maintained during the enzymatic procedure as well as throughout the gentle teasing of the tissue, until the cell can eventually be extracted and collected for mRNA analysis.

An intact, non-dissociated slice will be transferred onto the stage of a conventional microscope equipped with electrophysiological recording equipment and a perfusion chamber. Using either the "blind" or the "visual" patch technique, a fire-polished recording pipette will be used to patch on to the somatic membrane of a neuron. Either the whole-cell or the cell-attached patch configuration will be established, depending on the experimental design. Standard whole-cell pipette solution consists of (in mM): 140 $KMeSO_4$, 5 Hepes, 4 Tris ATP, 0.3 Tris GTP, 14 Tris-phosphocreatine and 0.1 Leupeptin. In current clamp mode, measures of AHP amplitudes, EPSPs, I/O curves, and $Na^+$ spike thresholds will be determined using an Axopatch 200 amplifier. After 10 min of baseline recording, an LTP protocol as described above will be used to induce long-term physiological changes. Cell electrophysiology will be monitored for an extra 20 minutes at which time, enzymatic treatment of the slice will be started within the perfusion chamber. After both sets of enzymes have been used (approximately 45 minutes), the slice will be gently teased-apart at the CA1 layer using glass prongs and fine micromanipulators to unmask the recorded cell. We have already attempted this approach several times and have successfully maintained input resistance of a recorded cell throughout the enzymatic and separation phase of the procedure.

For this approach, the slice must be held in place within the recording chamber and whole cell patch clamping must be maintained throughout the experiment. We currently hold the slice in place using a modified stimulating electrode. This tool is a four-pronged electrode array slightly curved to follow the curvature of the Schaffer collaterals. It is used as a cleat to hold the slice in place. Dorsally, will be embedded in the alveus of the hippocampal slice and attached to an electronically-controlled micromanipulator a fire-polished glass pipette. Teasing apart the slice will be accomplished by gently pulling the tissue in a dorsal/ventral direction using the glass pipette (thereby separating the cell layer). Both the glass pipette and the stimulus cleat will be positioned prior to patching and recording a cell. Cell harvesting will be accomplished as described previously. These studies will be conducted in parallel with those of the first approach outlined above, and will overlap in time and use the same animals.

c. Anticipated Outcomes: It is anticipated that one or the other of the above approaches will provide a successful method for performing physiological studies prior to partial dissociation and for the subsequent collection of the same cell after "unzipping". This seems likely because there are no major theoretical obstacles to these techniques, and the primary problems to overcome are those that will simply require time-consuming, trial-and-error studies to identify the most suitable methods. It is anticipated that after a few months, it will become clear whether the first or the second approach is the more promising, and we will then focus all development efforts on that approach. All of the necessary techniques are similar to those in routine use in our laboratories, and we have available upright and inverted imaging microscopes, as well as a range of patch clamp and current clamp amplifiers. Thus, it appears highly probable that these studies will yield a set of procedures, as well as electrophysiological criteria that will provide a standard means of conducting physiological studies prior to partial dissociation and single cell collection for RT-PCR.

Example 4

Separate Collection of Dendritic and Somatic Compartments for Selective PCR Analyses a. Rationale: Although the zipper slice procedure provides a means of collecting a neuron with its processes intact, there are no methods presently available for taking advantage of this intact collection procedure and analyzing the anatomical compartments separately. In this Example, we will develop methods for carefully dissecting the different cellular compartments. These studies will utilize the same animals, resources and schedule as in Example 3.

b. Methods: To control for the effects of transecting a cell into two components, one subset of recorded neurons will be collected intact as in the usual zipper preparation and analyzed for $\alpha_{1D}$ mRNA. A second set of cells will have the soma severed from the apical dendrite and both collected and processed separately. We will then recombine the results for $\alpha_{1D}$ mRNA from the severed components to determine whether cells that have had their processes severed lose transcript, or whether the sum of the two parts is, on average equivalent to values obtained in non-transected cells. In further studies, cells will be recorded from and extracted and the apical dendrite will be cut twice, once at the soma and again, approximately 150 microns above the cell soma. Each compartment will be analyzed by $\alpha_{1D}$mRNA content to determine whether the cutting process alters endogenous mRNA levels. In a separate set of experiments, primers for mRNA species that are known to be preferentially targeted to dendrites, such as ARC, MAP2 and CAMKIIα (Steward et al., 1998; Kuhl and Skehel, 1998) will be developed and used for RT-PCR analyses of gene expression. If the dissection process is accurate, these species should be found at much higher levels in dendritic vs. somatic fractions.

Figure 13:
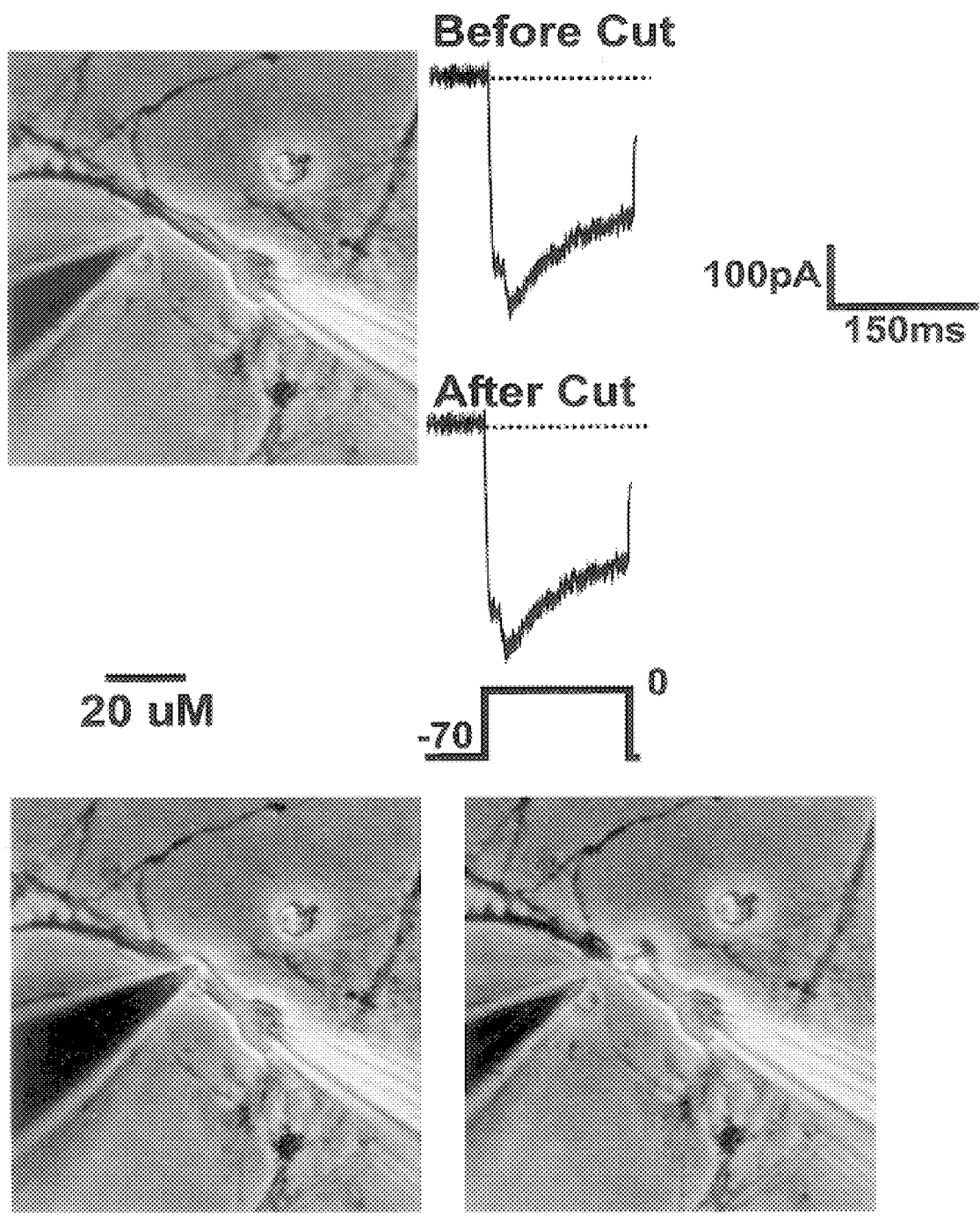
FIG. 13 shows transection of the major dendritic process of a hippocampal neuron in culture during simultaneous whole-cell patch clamp recording of $Ca^{2+}$ currents ($Na^+$ and $K^+$ currents blocked by TTX, TEA and Cs).

Cutting the processes. Our laboratory is highly experienced in ablating single apical dendrites from cultured hippocampal neurons. This can be done consistently while maintaining high resistance patch recording (cf. FIG. 13). Here, we propose to compare cutting with either 1) a glass pipette tool, 2) a sharp tungsten rod or 3) the harvesting pipette. For both 1) and 2), after the cell is extracted from the zipper slice, the dendrite will have to be lowered gently onto a substrate to provide mechanical support for transection. The bottom of the chamber would be used for this, employing either a jagged glass tool or a sharp tungsten rod to separate the two compartments. Each cell component would then be collected using an individual collecting pipette. For 3) we propose to follow our standard collection technique (cf. FIGS. 4, 10) but, in this case, when the collecting pipette draws the apical dendritic component of the recorded cell into its lumen, the collecting pipette will be raised such that the dendrite entering the harvesting pipette will be severed, a process that we will also facilitate by cutting with a micromanipulator-mounted glass tool. A second harvesting pipette will then collect the somatic component remaining on the recording pipette.

c. Possible Outcomes: These studies will compare possible methods for isolating separate compartments of a cell for independent gene expression analyses. They will be performed in rats and mice and should require about a year of trial-and-error experiments. At the end, they will have generated standard protocols for isolating single neuronal compartments for gene expression analyses. Most laboratories that perform single cell recording should be able to implement the protocols.

Example 5

Single Cell RNA Amplification and Gene Expression Profiling a. Rationale: One of the goals for this invention is to develop strategies for multiple gene expression analysis in single cells and, in particular, to establish methods for profiling differential gene expression in functionally characterized single neurons of hippocampal tissues from various age groups of animals. As noted above, the development of DNA microarrays or oligonucleotide chip technology has provided a powerful tool for simultaneous measurements of gene expression on a large-scale (reviewed in Jordan, 1998). The techniques involve labeling a complex cellular or tissue RNA sample and then using the probe to hybridize with sets of specific gene targets arrayed on either high-density membranes or solid glass support. Nevertheless, the techniques necessary for analyzing the small amounts of starting RNA material found in a single cell by these new methods are only beginning to be developed. The main challenge of single cell mRNA analysis is the generation of sufficient material for detecting specific mRNAs in the very small RNA pool of a single cell. This requires increasing the amount of labeled probes by amplifying the single cell mRNA pool.

For single cell mRNA amplification, two approaches have been developed: 1) Reverse transcription of cellular mRNA followed by polymerase chain reaction (RT-PCR) (reviewed in Monyer and Jonas, 1995); and 2) Linear antisense RNA amplification (aRNA) using RNA polymerase enzymes (Van Gelder et al., 1990; Eberwine et al., 1992). Both methods have been used in numerous studies on gene expression that analyzed individual single cells. The RT-PCR approach is highly sensitive for detection and quantitation of target mRNAs, providing that the primer sequences are known. The aRNA amplification method is very useful for expression profiling of multiple messages in single cells, and potentially can be applied to profile a large number of genes with the new cDNA microarray technology.

Kinetic single-target PCR methods were used for relative quantitation of differential gene expression among single cells (FIGS. 6, 7 and Chen et al., 1998). In our protocol, ⅕ of the single-cell cDNA from RT is used for PCR of a target message. Accordingly, up to 5 messages can be analyzed in a single cell. Among those studied to date are several rare messages (i.e., the L-type $Ca^{2+}$ channel subunits $\alpha_{1C}$, $\alpha_{1D}$ and $\beta_{1b}$), the $Ca^{2+}$ binding protein, calmodulin (CM), and an abundant "housekeeping" gene, glyceraldehyde-3-phosphate dehydrogenase (GAPDH). Although kinetic single-target RT-PCR has proven to be very sensitive and quantitative for our single-cell expression/function studies, it has the drawback that only a few genes can be analyzed per cell, under the current protocol.

The present invention expands the scope of these studies to correlate functional measurements with the expression of a large set of genes. The invention is directed to a protocol for single cell mRNA amplification that is compatible with collection of single neurons from zipper slices. The objectives will be to generate sufficient material for: (A) Performing large-scale quantitative kinetic PCR using gene-specific TaqMan probes for differential expression assays of multiple genes (for example multiple genes involved in cellular $Ca^{2+}$ regulation and/or $Ca^{2+}$ signaling pathway) using a 96-well real-time PCR instrument; and (B) Generation of fluorescent-labeled complex sample probes that are sufficient to hybridize with cDNA microarrays of expressed genes from a brain cDNA library.

b. Design: These studies will focus primarily on validating the proportional amplification methods under development. This will be accomplished by collecting multiple single neurons, and dividing the cDNA from RT into halves. One half of the cell will be used to estimate $\alpha_{1D}$ and CaM messages by our established quantitative kinetics PCR techniques (FIG. 7) and the other half will be amplified by the SMART PCR method (cf. below). After amplification the amplified cDNA will also be analyzed for expression of the same two messages (as well as others), by our quantitative real-time PCR system, with gene specific TaqMan probes (cf. below).

The validation of proportional amplification will be tested by individual cell correlations between values obtained directly by single target PCR and the values obtained following SMART PCR amplification. Separate correlations will be run for $\alpha_{1D}$ and CaM. If the amplification is reliable and proportional, then it should be predicted that highly significant correlations will be found. These tests will be performed in 15 young, 15 mid-aged and 15 aged rat neurons, to determine whether aging alters the stability or accuracy of amplification. A mid-aged group will be included in these studies to provide a careful assessment across the full age range.

If the SMART PCR method proves unreliable, the same amplification studies will be repeated with the aRNA method. Once a successful amplification technique is developed for rats, we will then carry out similar studies in young and aged mice. Following verification of the methods in mice, we will examine large scale expression profiling on Affymetrix cDNA microarray chips for mouse. The cDNA databases will be searched and the mouse microarray (for example, GeneChip Murine 19K subB Array) containing those $Ca^{2+}$ relevant cDNAs in which we are most interested will be tested in 5 separate tests comparing young and aged neurons. Again, results will be validated for selected genes by target-specific PCR and subsequent correlation analyses between the two procedures across the same cells.

c. Methods for Single-Cell mRNA Amplification: The hippocampal "zipper" slice preparation will be used for the isolation of individual live neurons, as described previously, and an entire neuron will be harvested with a capillary microelectrode, immediately placed into a chilled microcentrifuge tube containing 20U RNAse inhibitor in 5 ul solution, and processed for cDNA synthesis. The cellular RNA of each single neuron is converted to cDNA by reverse transcription using MMLV reverse transcriptase and a synthetic oligonucleotide primer.

Two methods for single-cell mRNA amplification. In one established procedure for single neuron linear aRNA amplification (Eberwine et al., 1992), a synthetic primer containing oligo $(dT)_{15}$ and the T7 RNA polymerase binding sequence attached at its 5'-end, i.e. oligo(dT)-T7, is used in the RT reaction. The RT is followed by second strand cDNA synthesis and the purified cDNA is then transcribed with T7 RNA polymerase yielding amplified antisense RNA pool. The aRNA can be labeled and used to hybridize with gene specific cDNA clones by reverse Northern or Southern blotting. It is estimated that one round of aRNA synthesis can generate about 2000-fold of the original RNA pool and usually two rounds of aRNA synthesis are used for expression profiling, as carried out in several studies (Eberwine et al., 1992; Mackler et al., 1992; Mackler and Eberwine, 1993; Crino and Eberwine, 1996; Cheetham et al., 1997; Nair et al., 1998; Callahan et al., 1998; Chow et al., 1998). Although the aRNA amplification method is very useful for single cell RNA analysis, it remains to be determined whether two rounds of aRNA amplification can generate sufficient substrate for detectable hybridization signals on new cDNA microarrays, particularly for rare messages.

Very recently, however, an alternative PCR-based cDNA amplification approach to generating an amplified cDNA pool was described (Endege et al., 1999). In this recent report, Endege and colleagues demonstrated that using the SMART PCR cDNA Synthesis Method (CLONTECH) the high-, medium- and low-abundance transcripts in the original RNA profile of biopsy samples could be amplified representatively in the resulting cDNA. Moreover, the PCR amplified cDNA can be used as complex probes for differential gene expression profiling. This PCR cDNA amplification method uses a modified oligo(dT) primer and a special designed 5' primer in reverse transcription; during the single strand cDNA synthesis, the 5' primer serves as an extended template at the 5' end of the RNAs to allow continuation of transcription to the end of the primer by a Switch Mechanism At 5' end of RNA Transcripts (SMART) of the RT enzyme(CLONTECH). The resulting cDNA often contains the full-length transcript with the 5'-primer sequence added at the end which then serves as a universal priming site for subsequent PCR amplification. Using 1 $\mu$m of starting tissue RNA, approximately 1.25 to 1.75 mg of PCR amplified cDNA was obtained under optimized conditions, i.e. optimal PCR cycles for maximum yield of full length cDNAs (Endege et al., 1999). Moreover, as little as 50 ng of the amplified cDNA was needed for generating complex probes for expression profiling and maintaining sensitivity for low abundance messages.

Either the aRNA amplification or SMART PCR cDNA synthesis methods appear applicable for the single cell RNA amplification that is necessary prior to large scale gene expression profiling. However, since our current single-cell gene expression studies use PCR-based single-target RT-PCR assays, we propose here to adapt the PCR cDNA synthesis approach for our studies requiring RNA amplification of single neurons. Individual neurons collected after functional characterizations will be processed for cDNA synthesis and amplification using the reagents from the SMART PCR cDNA synthesis kit (CLONTECH). The manufacturer's instructions will be followed with modifications adjusted for our single cell protocols, (i.e. the entire cell will be used in each RT reaction using the 3' and 5' primers provided in the kit, followed by cDNA PCR amplification using the primers and instructions in the manual). Optimal PCR conditions, e.g. number of cycles, will be determined by monitoring the kinetics of GAPDH cDNA synthesis as described in Endege et al. (1999). As noted, to validate that the original expression profile in a cell is proportionally represented in the PCR-amplified cDNA using the SMART protocol, we will analyze in parallel the expression of VSCC $\alpha_{1D}$, $\beta$ and CaM messages before and after amplification, using our established quantitative kinetics PCR procedures (see Preliminary data) on subfractions of cellular RNA samples.

Analysis of Multiple Gene Expression by Two Approaches: 1) 96-well PCR; and 2) cDNA Microarrays Approach #1: Differential expression of multiple messages in single cells by large scale multiple single-target RT-PCR using gene specific TagMan probes and quantitative real-time PCR. For differential expression profiling of an intermediate-scale number of genes, (e.g., a limited series of genes for cellular $Ca^{2+}$ regulation and $Ca^{2+}$ signaling), in single neurons, we will use the real-time PCR system (ABI 7700 PE Biosystem, 96-well) for quantitative single-target PCR, and will analyze in parallel multiple messages in individual cells. RNA of a single cell will be amplified by PCR cDNA synthesis (as described in the previous section) and aliquots will be added to individual wells, each of which will contain a message-specific TaqMan probe and primers for gene-specific PCR. The basic steps of this approach are as follows:

Single cell RNA amplification by PCR cDNA synthesis. In our current single-cell RT-PCR protocol, the cDNA of a single cell is aliquoted in amount suitable for analyzing up to 4–5 messages, including several rare messages (<0.01% of the total RNA). These rare messages such as VSCC subunits, require two-step PCR. As noted above, to be able to analyze a larger number of messages from one cell than we are capable of at present, will require amplification of the single cell RNA pool. Thus, each single neuron collected in the present studies will be used for RT, followed by PCR cDNA amplification using the SMART PCR cDNA synthesis reagents (CLONTECH) and modified procedures as described in the previous section. However, if this procedure does not prove suitable, we will use the aRNA amplification method. Although the latter may not generate enough probe for the cDNA microarrays, it is almost certain to be able to provide sufficient substrate for this multiple single message PCR approach.

Multiple single-target PCR with gene specific TaqMan probes. Aliquots of an amplified cDNA pool from a single cell will be analyzed for the message level of multiple genes by quantitative real-time PCR. In a 96-well format, up to 48 messages can be analyzed with replicates in the adjacent wells. When running parallel PCR on multiple genes, it is essential that each gene specific probe and primers are selected for comparable PCR conditions, i.e. similar GC% in the primer sequences so that a similar annealing temperature can be used in a run. The selection of primers is also crucial to ensure specificity for the target message and to avoid complementary sequences within and among primers. The optimal PCR conditions for a set of primers and probes and its target specificity will be determined prior to performing multiple PCR.

These methods could be used to investigate multiple gene expression with aging, in an experimental scheme of using a 96-well format to compare expression profile of a set of genes among cells from 3 different age groups (e.g., young, mid-aged and aged). Aliquots of amplified cDNA of a cell will be added to each of 32 wells, each of which contained a message-specific TaqMan probe and primers placed in replicates between adjacent wells. The 16 messages to be analyzed in parallel will be grouped for comparable PCR conditions so that the reactions can be run at the optimal settings, e.g. the annealing temperature, cycle numbers, etc. The same design will be repeated 15 times for a set of three cells from three animals (e.g., one of each age group) at a time, so that data eventually can be obtained on 15 cells from each group for statistical analysis.

Alternatively, we will also perform experiments using a scheme in which one message is assessed at a time in multiple cells from each age group. For example, using a 96-well format, 15 cells of each age group will be analyzed in duplicates, plus the control samples for a single message. In this scheme, sufficient data can be obtained for statistical analysis of differential expression for a specific message on each run.

Comparative real-time PCR quantitation. The use of fluorescent-labeled TaqMan probes allows real-time measurements of the accumulation of target-specific PCR products during an ampliication process. Quantitation by TaqMan real-time PCR is obtained by monitoring the accumulation of fluorescence signals during PCR. The real-time PCR device (PE Biosystems ABI 7700) makes it possible to obtain large-scale PCR kinetics on 96 individual reactions simultaneously. Data processing is performed by the software of the 7700 system and calculation of the initial amount of a target message using a standard curve can be obtained.

Approach #2: cDNA microarray hybridization and expression profiling. For large-scale gene expression profiling, the current protocols for cDNA microarray hybridizations require labeled complex cellular cDNA probes in the nanogram to microgram range, even in conditions using highly sensitive two-fluorescence labeling (Schena, 1995). To develop a protocol for microarray expression profiling in single neurons, our initial experiments will determine whether sufficient probe can be generated from a single neuron using the SMART PCR cDNA amplification procedure described above. If this proves too erratic or variable, we will then also examine the aRNA amplification method. Only single neurons collected from mouse hippocampal preparations will be tested in the microarray studies, as the mouse cDNA GeneChip arrays are currently commercially available (Affymetrix). The basic procedures for this approach are outlined below:

Fluorescent probe synthesis. In a gene microarray hybridization scheme, the labeled probe comprises the complex cDNA copies obtained from cellular mRNAs. The complex probe is then used to hybridize with cDNA clones of many target genes arrayed on a solid support (Ramsay, 1998). Thus, signal production from each clone in an array is governed by the abundance of individual message present in the complex probe (reviewed in Jordan, 1998; Duggan et al., 1999). For microarray assays of single cell RNA, the mRNA pool, as noted, must first be amplified proportionally either by linear aRNA amplification or the SMART PCR cDNA synthesis procedure. In the proposed studies, the amplified cDNA or aRNA will be used to generate fluorescent-labeled complex probes for hybridization with murine cDNA library microarrays.

To generate a complex cDNA probe, we will use fluorescent labeling and the two-color fluorescent probe hybridization procedure (Schena et al., 1996) to assess differential expression in RNA samples from at least two different age groups. The amplified cDNA or aRNA of a cell will be labeled using a fluorescence-tagged nucleotide analog, i.e. Cy3- or Cy5-dCTP (Heller et al., 1997) added in the RT or in the RT random priming (Stratagene) procedure. Two fluorophores will be used to independently label samples of two age groups. The two probes will be mixed in equivalent concentrations, and hybridized simultaneously to a microarray derived from a hippocampal or brain cDNA library. To reduce cost at this stage of technical development, the microarray that is commercially available (Affymetrix) can be used. A control yeast mRNA, e.g. trp4 gene for tryptophan biosynthesis, will be added at a known dilution concentration in each RT labeling reaction to provide an internal standard for calibration (Schena et al., 1995).

Probe hybridization and quantitation. The use of glass slide microarrays requires a very small hybridization volume and a resulting high probe concentration in the reaction mixture, thus providing high sensitivity of the assay (Schena et al., 1995). At this stage of technical development, the GeneChip murine cDNA arrays (Affymetrix) can be used for hybridization of mouse cellular complex probes. The probe hybridization and detection will be carried out following the manufacturer's protocols (Affymetrix).

Data Analysis. Analysis of cDNA microarrays will depend on laser scanning activation of fluorescence with complex software packages for detecting differential signals above background noise (e.g., Hewlett-Packard GeneScan and Workstation with Analysis Suite, Affymetrix).

Utility

The most apparent use is for research purposes. Because of the advantages outlined above, research on gene and other molecular regulation, on phenotypic consequences of gene activity and on drug discovery, among many others, could be enhanced.

However, because the method promises to provide more accurate quantitative estimates of molecular species in a clearly identified cell type, it is also possible that the method will be advantageous for clinical diagnostic purposes, for example, in detecting genetic or biochemical defects, tissue compatibilities for transplants, identifying candidates for therapeutic regimens, and many other possibilities.

In addition, the method could eventually be useful in therapeutic approaches, by allowing the accurate characterization of subcellular function in specific individuals, thereby allowing more accurate selection of treatment or more refined implementation of gene transfer, pharmacological or other treatments, among other possibilities.

Whereas particular embodiments of this invention have been described above for purposes of illustration, it will be evident to those persons skilled in the art that numerous variations of the details of the present invention may be made without departing from the invention as defined in the appended claims. All of the references cited herein are incorporated by reference in their entirety.

REFERENCES

Baro D J, Levini R M, Kim M T, Willms A R, Lanning C C, Rodriguez H E, Harris-Warrick R M. Quantitative single-cell-reverse transcription-PCR demonstrates that A-current magnitude varies as a linear function of ain shal gene expression in identified stomatogastric neurons. J Neurosci 17:6597–6610, 1997.

Blalock E M, Chen K-C, Landfield P W, Slevin J T. Correlated changes in L-type $Ca^{2+}$ channel activity and $\alpha_{1D}$ain mRNA levels in individual neurons of kindled rats. (In Preparation)

Bowers G, Cullinan W E, Herman J P. Region-specific regulation of glutamic acid decarboxylase (GAD) mRNA expression in central stress circuits. J Neurosci 18:5938–47, 1998.

Callahan L M, Chow N, Cheetham J E, Cox C, Coleman P D. Analysis of message expression in single neurons of Alzheimer's disease brain. Neurobiol Aging 19:99–105, 1998.

Cheetham J E, Coleman P D, Chow N. Isolation of single immunohistochemically identified whole neuronal cell bodies from post-mortem human brain for simultaneous analysis of multiple gene expression. J Neurosci. Methods 77:43–48; 1997.

Chen K-C, Kaminker P G, Blalock E M, Thibault O, Landfield P W. Single-cell RT-PCR and single $Ca^{2+}$ channel recording in adult and aged "zipper" hippocampal slices. Soc Neurosci Abs 24:1972, 1998.

Chen K-C, Blalock E M, Landfield P W. Correlation of L-type $Ca^{2+}$ current amplitude with the $\alpha_{1D}$ mRNA level in single neurons from hippocampal zipper slice preparation. (In preparation).

Chiang L W. Detection of gene expression in single neurons by patch-clamp and single-cell reverse transcriptase polymerase chain reaction. J Chromatogr 806:209–218, 1998.

Chow N, Cox C, Callahan L M, Weimer J M, Guo L, Coleman P D. Expression profiles of multiples genes in single neurons of Alzheimer's disease. Proc Natl Acad Sci 95:9620–9625, 1998.

Crino P B, Eberwine J. Molecular characterization of the dendritic growth cone: regulated mRNA transport and local protein synthesis. Neuron 17:1173–1187, 1996.

Cullinan W E, Herman J P, Watson S J. Ventral subicular interaction with the hypothalamic paraventricular nucleus: Evidence for a relay in the bed nucleus of the stria terminalis. J Comp Neurol 332:1–20, 1993.

Davis W P, Janssen Y M, Mossman B T, Taatjes D J. Simultaneous triple fluorescence detection of mRNA localization, nuclear DNA, and apoptosis in cultured cells using confocal scanning laser microscopy. Histochem Cell Biol 108: 307–11,1997.

Dirks R W, Raap A K. Cell-cycle-dependent gene expression studied by two-colour fluorescent detection of a mRNA and histone mRNA. Histochem Cell Biol 104: 391–5, 1995.

Duggan D G, Bittner M, Chen Y, Meltzer P, Trent J M. Expression profiling using cDNA microarrays. Nat Genet Supplement 21:10–14, 1999.

Eberwine J, Yeh H, Miyashiro K, Cao Y, Nair S, Finnell R, Zeftel M, Coleman P. Analysis of gene expression in single live neurons. Proc Natl Acad Sci 89:3010– 3014, 1992.

Endege W O, Steinmann K E, Boardman L A, Thibodeau S N, Schlegel R. Representative cDNA libraries and their utility in gene expression profiling. BioTechniques 26:542–550, 1999.

Giese K P, Fedorov N B, Filipkowski R K, Silva A J. Autophosphorylation at Thr286 of the alpha calcium-calmodulin kinase II in LTP and learning. Science 279:870–873, 1998.

Gray R, Fisher R, Spruston N, Johnston D. Acutely exposed hippocampal neurons: A preparation for patch clamping neurons from adult hippocampal slices. In *Preparations of Vertebrate Central Nervous System In Vitro*, Ed. H Jahnsen 324, 1990.

Guthrie P B, Segal M, Kater S B. Independent regulation of calcium revealed by imaging dendritic spines. Nature 354:76–80, 1991.

Heller R N, Schena M, Chai A, Shalon D, Bedilion T, Gilmore J, Woolley D E, Davis R W. Discovery and analysis of inflammatory disease-related genes using cDNA microarrays. Proc Natl Acad Sci USA 94: 2150–2155, 1997.

Herman J P, Kwak S P, Watson S J. Hybridization approaches to the study of adrenocorticosteroid receptors in the CNS. In dekloet ERSutanto W (Eds.), Neurobiology of Steroids, Academic Press Orlando pp. 189–210, 1994.

Herman J P, Dolgas C M, Marcinek R, Langub M C Jr. Expression and glucocorticoid regulation of natriuretic peptide clearance receptor (NPR-C) mRNA in rat brain and choroid plexus. J Chem Neuroanat; 11: 257–65, 1996.

Herman J P, Morrison D G. Immunoautoradiographic and in situ hybridization analysis of corticotropin-releasing hormone biosynthesis in the hypothalamis paraventricular nucleus. J Chem Neuroanat 11: 49–56, 1996.

Herman J P, Spencer R. Regulation of hippocampal glucocorticoid receptor gene transcription and protein expression in vivo. J Neurosci 18: 7462–73, 1998.

Herman J P, Chen K-C, Booze R M, Landfield P W. Upregulation of $\alpha_{1D}$ Ca2+ channel subunit mRNA expression in the hippocampus of aged F344 rats. Neurobiol Aging 19: 581–587, 1998.

Jonas P, Racca C, Sakmann B, Seeburg P H, Monyer. Differences in $Ca^{2+}$ permeability of AMPA-type glutamate receptor channels in neocortical neurons caused by differential GluR-B subunit expression. Neuron 12:1281–1289, 1994.

Johnston A R, Black C, Fraser j, MacLeod N. Scrapie infection alters the membrane and synaptic properties of mouse hippocampal CA1 pyramidal neurones. J Physiol 1:500 (Pt 1): 1–15, 1997.

Jordan B R. Large-scale expression measurement by hybridization methods: from high-density membranes to "DNA chips". J Biochem 124:251–258; 1998.

Kerr D S, Campbell L W, Hao S-Y, Landfield P W. Corticosteroid modulation of hippocampal potentials: increased effect with aging. Science 245:1505–1509, 1989.

Kirkwood A, Silva A, Bear M F. Age-dependent decrease of synaptic plasticity in the neocortex of αCaMKII mutant mice. Proc Natl Acad Sci 94:3380–3383, 1997.

Kuhl D, Skehel P. Dendritic localization of mRNAs. Curr Opin Neurobiol 8:600–606, 1998.

Landfield P W, Thibault O, Mazzanti M L, Porter N M, Kerr D S. Mechanisms of neuronal death in brain aging and Alzheimer's Disease: Role of endocrine-mediated calcium dyshomeostasis. J Neurobiol 23:1247–1260, 1992.

McKay J A, Murray G I, Keith W N, McLeod H L. Amplification of fluorescent in situ hybridisation signals in formalin fixed paraffin wax embedded sections of colon tumour using biotinylated tyramide. Mol Pathol 50:322–5,1997.

Mackler S A, Brooks B P, Eberwine J H. Stimulus-induced coordinate changes in mRNA abundance in single postsynaptic hippocampal CA1 neurons. Neuron 9:539–548, 1992.

Mackler S A, Eberwine J H Diversity of glutamate receptor subunit mRNA expression within live hippocampal CA1 neurons Mol Pharm 44:308–315,1993.

Monyer H, Jonas P. Polymerase chain reaction analysis of ion channel expression in single neurons of brain slices. In: Sakmann B, Neher E. (Eds.) Single Channel Recording, New York, Plenum Press, pp. 357–373, 1995.

Monyer H, Lambolez B. Molecular biology and physiology at the single-cell level. Curr Opin Neurobiol 5:382–387, 1995.

Nair S M, Werkman T R, Craig J, Finnell R, Joels M, Eberwine J H. Corticosteroid regulation of ion channel conductances and mRNA levels in individual hippocampal CA1 neurons. J Neurosi 18:2685–2696, 1998.

Paradies M A, Steward O. Multiple subcellular mRNA distribution patterns in neurons: a nonisotopic in situ hybridization analysis. J Neurobiol 33:473–493, 1997.

Perez-Reyes E, Wei X Y, Castellano A, Birnbaumer L. Molecular diversity of L-type calcium channels. Evidence for alternative splicing of the transcripts of three non-allelic genes. J Biol Chem 265:20430–6, 1990.

Porter N M, Angelotti T P, Twyman R E, Macdonald R L. Kineticproperties of $\alpha_1\beta_1$-aminobutyric $acid_A$ receptor channels expressed in chinese hamster ovary cells: regulation by pentobarbital and picrotoxin. Mol Pharmacol 42:872–881, 1992.

Porter N M, Thibault O, Thibault V, Chen K C, Landfield P W. Calcium channel density and hippocampal cell death with age in long-term culture. J Neurosci 17: 5629–39, 1997.

Raap A K. Advances in fluorescence in situ hybridization. Mutat Res 400:287–98, 1998.

Ramsay G. DNA chips: state-of-the art. Nat Biotechnol 16:40–44,1998.

Schena M, Shalon D, Davis R W, Brown P O. Quantitative monitoring of gene expression patterns with a complementary DNA microarray. Science 270:467–470,1995.

Schena M, Shalon D, Heller R, Chai A, Brown P O, Davis R W. Parallel human genome analysis: microarray-based expression monitoring of 1000 genes. Proc Natl Acad Sci 93:10614–10619, 1996.

Speel E J, Hopman A H, Komminoth P. Amplification methods to increase the sensitivity of in situ hybridization: play card(s). J Histochem Cytochem 47:281–8,1999.

Speel E J, Saremaslani P, Roth J, Hopman A H, Komminoth, P. Improved mRNA in situ hybridization on formaldehyde-fixed and paraffin-embedded tissue using signal amplification with different haptenized tyramides. Histochem Cell Biol 110: 571–7,1998.

Sudweeks S, Twyman R E. Single cell reverse transcription-polymerase chain reaction (RT-PCR) and the gabaa receptor. Neurochem Int 2:137–139, 1996.

Tank D W, Sugimori M, Connor J A, Llinas R R. Spatially resolved calcium dynamics of mammalian purkinje cells in cerebellar slices. Science 242:773–777, 1988.

Thibault O, Mazzanti M L, Blalock E M, Porter N M, Landfield P W. Single-channel and whole-cell studies of calcium currents in young and aged rat hippocampal slice neurons. J Neurosci Meth 59:77–83, 1995a.

Thibault O, Porter N M, Mazzanti-Rose M L, Campbell L W, Blalock E M, Landfield P W. Dual patch pipefte recordings in hippocampal neurons: evidence that long $Ca^{2+}$ tail currents reflect $Ca^{2+}$ channel activity at resting potential. Soc Neurosci Abs 21:1577, 1995b.

Thibault O, Landfield P W. Increase in single L-type calcium channels in hippocampal neurons during aging. Science 272:1017–20,1996.

Thibault O, Porter N M, Chen K-C, Blalock E M, Kaminker P G, Clodfelter G V, Brewer L D, Landfield P W. Calcium dysregulation in neuronal aging and Alzheimer's disease: History and new directions. Cell Calcium 24:417–433, 1998a.

Thibault O, Clodfelter G V, Landfield P W. $Ca^{2+}$ transients during synaptic activation in hippocampal sliceneurons of adult and aged rats. Soc Neurosci Abs 24:1971, 1998b.

Tkatch T, Baranauskas G, Surmeier D J. Single cell RT-PCR demonstrates a linear relationship between a-like current and KV4.2 expression in striatal and pallidal cell types. Soc Neurosci Abst 24:1330, 1998.

Van Gelder R N, Von Zastrow M E, Yool A, Dement W C, Barchas J D, Eberwine J H. Amplified RNA synthesized from limited quantities of heterogeneous cDNA. Proc Natl Acad Sci 87:1553–1667, 1990.

Watson A, Mazumder A, Stewart M, Balasubramanian S. Technology for microarray analysis of gene expression. Curr Opin Biotechnol 9:609–614,1998.

Winder D G, Mansuy I M, Osman M, Moallem T M, Kandel E R. Genetic and pharmacological evidence for a novel, intermediate phase of long-term potentiation suppressed by calcineurin. Cell 92:25–37, 1998.

We claim:

1. A method of isolating and harvesting a substantially intact single cell from its organ tissue comprising the following steps:
   (i) subjecting a tissue mass to a dissociation method so that the cells are dissociated from the tissue to expose cell bodies or cell processes;
   (ii) contacting a dissociated cell on its membrane with a device capable of collecting the cell substantially intact from said tissue;
   (iii) withdrawing said device with the cell attached; and
   (iv) harvesting said cell, wherein said cell is isolated intact from its organ tissue.

2. The method according to claim 1, wherein said harvesting step comprises collecting the cell by drawing the cell into the lumen of a second collection device.

3. The method according to claim 1, wherein the cells are partially dissociated from the tissue.

4. The method according to claim 1, wherein said tissue is a part of the central nervous system.

5. The method according to claim 4, wherein said tissue is hippocampal tissue.

6. The method according to claim 5, wherein said tissue is a partially dissocated hippocampal "zipper" slice.

7. The method according to claim 6, wherein said cell is a neuron.

8. The method according to claim 1, wherein step (ii) comprises patching a first glass pipette onto the cell, wherein a negative pressure is maintained on the cell membrane through the glass pipette, and a tight seal is formed between the cell membrane and the pipette.

9. The method according to claim 1, wherein said device is a suction pipette or a sharp dissecting needle.

10. A method for obtaining molecules from a single cell comprising:
    (i) isolating a substantially intact single cell from its organ tissue comprising the following steps:
       (a) subjecting a tissue mass to a dissociation method so that the cells are dissociated from the tissue to expose cell bodies or cell processes;
       (b) contacting a dissociated cell on its membrane with a device capable of collecting the cell substantially intact from said tissue;
       (c) withdrawing said device with the cell attached; and
    (ii) isolating or detecting said molecules in the single cell.

11. The method according to claim 10, wherein said molecule is nucleic acid, proteins, lipids, carbohydrates or any other biochemical substance present in the cell.

12. The method according to claim 11, wherein said nucleic acid is mRNA.

13. The method according to claim 12, wherein said mRNA is detected by amplification through polymerase chain reaction.

14. The method according to claim 10, wherein said molecule is detected by hybridization, autoradiography, fluorescence, protein ligand interaction, or immunocytochemistry.

15. The method according to claim 10, wherein said harvesting step comprises collecting the cell by drawing the cell into the lumen of a second collection pipette.

16. The method according to claim 10, wherein the cells are partially dissociated from the tissue.

17. The method according to claim 10, wherein said tissue is a part of the central nervous system.

18. The method according to claim 15, wherein said tissue is hippocampal tissue.

19. The method according to claim 10, wherein said tissue is a partially dissocated hippocampal "zipper" slice.

20. The method according to claim 18, wherein said cell is a neuron.

21. The method according to claim 10, wherein the isolated cell is said single cell is assayed for functional activity before or after disrupting the membrane in step (ii).

22. The method according to claim 10, wherein step (ii) further comprises dissecting, amputating or isolating a portion of the cell and measuring the molecular content of said portion.

23. The method according to claim 10, wherein said single cell is mixed with other single cells to obtain a plurality of single cells.

24. The method according to claim 10, wherein step (i)(b) comprises patching a first glass pipette onto the cell, wherein a negative pressure is maintained on the cell membrane through the glass pipette, and a tight seal is formed between the cell membrane and the pipette.

25. The method according to claim 10, wherein said device is a suction pipette or a sharp dissecting needle.

26. The method according to claim 10, wherein said detection is carried out in a microarray system.

27. A method for measuring a molecule(s) from a single cell comprising:
    (i) isolating and harvesting a substantially intact single cell from its organ tissue comprising the following steps:
       (a) subjecting a tissue mass to a dissociation method so that the cells are dissociated from the tissue to expose cell bodies or cell processes;
       (b) contacting a dissociated cell on its membrane with a device capable of collecting the cell substantially intact from said tissue;
       (c) withdrawing said device with the cell attached;
       (d) harvesting said cell, wherein said cell is isolated intact from its organ tissue; and
    (ii) measuring said molecule(s) in the single cell.

28. The method according to claim 27, wherein said molecule is nucleic acid, proteins, lipids, carbohydrates or any other biochemical substance present in the cell.

29. The method according to claim 27, wherein said nucleic acid is mRNA.

30. The method according to claim 27, wherein said harvesting step comprises collecting the cell by drawing the cell into the lumen of a second collection pipette.

31. The method according to claim 27, wherein the cells are partially dissociated from the tissue.

32. The method according to claim 27, wherein said tissue is a part of the central nervous system.

33. The method according to claim 32, wherein said tissue is hippocampal tissue.

34. The method according to claim 27, wherein said tissue is a partially dissociated hippocampal "zipper" slice.

35. The method according to claim 33, wherein said cell is a neuron.

36. The method according to claim 27, wherein the isolated cell is assayed for functional activity before or after disrupting the membrane in step (ii).

37. The method according to claim 27, wherein a portion of the cell is dissected, amputated or isolated to measure the molecular content in the dissected portion of the cell.

38. The method according to claim 27, wherein said single cell is mixed with other single cells to obtain a plurality of single cells.

39. The method according to claim 27, wherein step (i)(b) comprises patching a glass pipette onto the cell, wherein a negative pressure is maintained on the cell membrane through the glass pipette, and a tight seal is formed between the cell membrane and the pipette.

40. The method according to claim 27, wherein said device is a suction pipette or a sharp dissecting needle.

* * * * *